(12) United States Patent
Giraud et al.

(10) Patent No.: US 10,059,047 B2
(45) Date of Patent: *Aug. 28, 2018

(54) INJECTION MOLDING PROCESSES FOR MOLDING BARREL AND THERMOPLASTIC SYRINGES HAVING LOW AXIAL DRAFT ANGLES

(71) Applicant: SiO2 Medical Products, Inc., Auburn, AL (US)

(72) Inventors: Jean-Pierre Giraud, Auburn, AL (US); Bruce Rabinne, Boissey-le-Chatel (FR); Herve Pichot, Chenneviere-sur-Marne (FR)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 36 days.

This patent is subject to a terminal disclaimer.

(21) Appl. No.: 15/266,208

(22) Filed: Sep. 15, 2016

(65) Prior Publication Data
US 2017/0066171 A1 Mar. 9, 2017

Related U.S. Application Data

(63) Continuation of application No. 13/809,455, filed as application No. PCT/US2011/044215 on Jul. 15, 2011, now Pat. No. 9,475,225.
(Continued)

(51) Int. Cl.
B29C 45/73 (2006.01)
A61B 5/15 (2006.01)
(Continued)

(52) U.S. Cl.
CPC ............ *B29C 45/73* (2013.01); *A61B 5/1438* (2013.01); *A61B 5/15003* (2013.01); *A61B 5/153* (2013.01); *A61B 5/154* (2013.01); *A61B 5/150236* (2013.01); *A61B 5/150244* (2013.01); *A61B 5/150259* (2013.01); *A61B 5/150274* (2013.01); *A61B 5/150351* (2013.01); *A61B 5/150389* (2013.01); *A61B 5/150519* (2013.01); *A61M 5/178* (2013.01); *A61M 5/3129* (2013.01); *A61M 5/3137* (2013.01); *A61M 5/31511* (2013.01); *A61M 5/343* (2013.01); *B29C 45/0001* (2013.01); *B29C 45/0053* (2013.01); *B29C 45/261* (2013.01); *B29C 45/40* (2013.01); *B29C 45/78* (2013.01); *C23C 16/042* (2013.01); *C23C 16/345* (2013.01); *C23C 16/401* (2013.01); *C23C 16/50* (2013.01); *C23C 16/505* (2013.01); *A61M 5/31513* (2013.01); *A61M 2005/3131* (2013.01);
(Continued)

(58) Field of Classification Search
CPC .......... A61B 5/15002; A61B 5/150015; A61B 5/15003; A61B 5/150236; A61B 5/153; A61M 5/1782; A61M 5/1785; A61M 5/3129; A61M 2005/3131; A61M 2005/3132; B29C 45/261; B29C 2045/4089
See application file for complete search history.

(56) References Cited

U.S. PATENT DOCUMENTS

2005/0033237 A1\* 2/2005 Fentress ............ A61M 25/0009
604/165.03

\* cited by examiner

*Primary Examiner* — Stella K Yi
(74) *Attorney, Agent, or Firm* — David B Gornish

(57) ABSTRACT

Methods of molding a barrel, such as a syringe barrel having very low draft, are disclosed. Thermoplastic syringes having very low interior draft angels are also disclosed.

20 Claims, 24 Drawing Sheets

Related U.S. Application Data

(60) Provisional application No. 61/365,277, filed on Jul. 16, 2010, provisional application No. 61/413,329, filed on Nov. 12, 2010.

(51) Int. Cl.

| | |
|---|---|
| *A61B 5/153* | (2006.01) |
| *A61B 5/154* | (2006.01) |
| *A61M 5/31* | (2006.01) |
| *A61M 5/315* | (2006.01) |
| *B29C 45/00* | (2006.01) |
| *B29C 45/26* | (2006.01) |
| *B29C 45/40* | (2006.01) |
| *B29C 45/78* | (2006.01) |
| *C23C 16/04* | (2006.01) |
| *C23C 16/34* | (2006.01) |
| *C23C 16/40* | (2006.01) |
| *C23C 16/505* | (2006.01) |
| *A61M 5/178* | (2006.01) |
| *A61M 5/34* | (2006.01) |
| *C23C 16/50* | (2006.01) |
| *B29L 31/00* | (2006.01) |
| *B29K 23/00* | (2006.01) |
| *B29K 55/00* | (2006.01) |

(52) U.S. Cl.
CPC . *A61M 2005/3139* (2013.01); *A61M 2207/00* (2013.01); *A61M 2207/10* (2013.01); *B29C 2045/0079* (2013.01); *B29C 2045/4063* (2013.01); *B29C 2045/7343* (2013.01); *B29C 2045/7393* (2013.01); *B29K 2023/06* (2013.01); *B29K 2023/12* (2013.01); *B29K 2055/00* (2013.01); *B29K 2995/0012* (2013.01); *B29L 2031/7544* (2013.01)

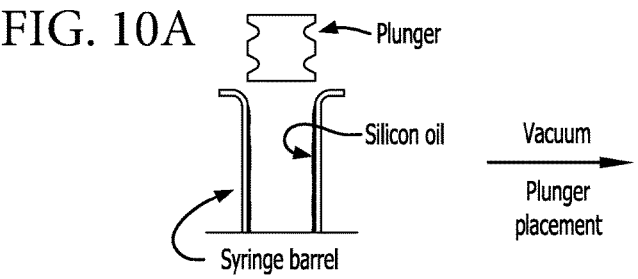
FIG. 10A
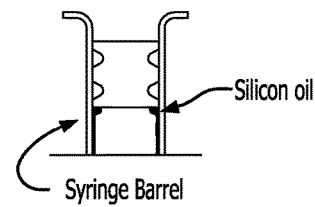
FIG. 10B
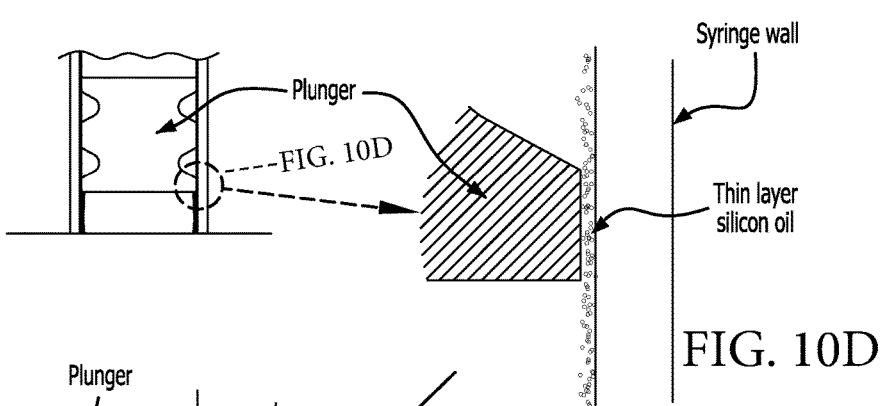
FIG. 10C
FIG. 10D
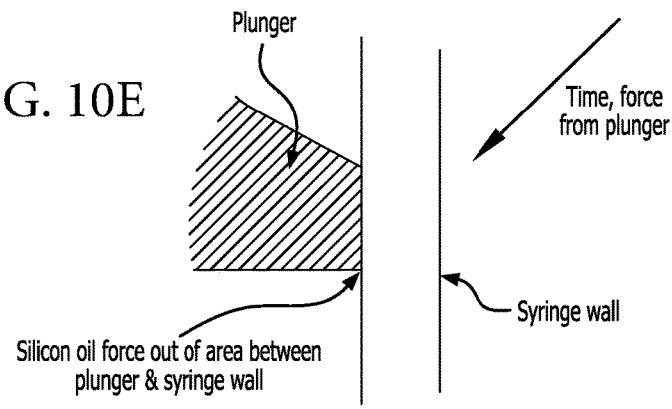
FIG. 10E
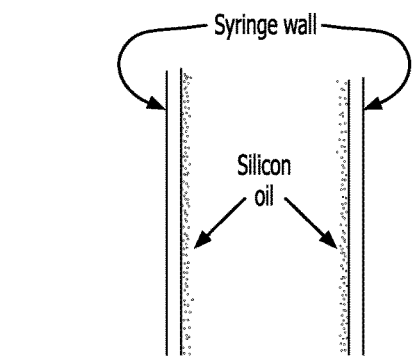
FIG. 10F
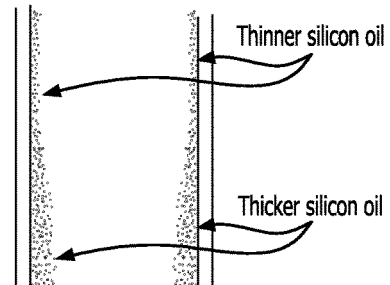
FIG. 10G

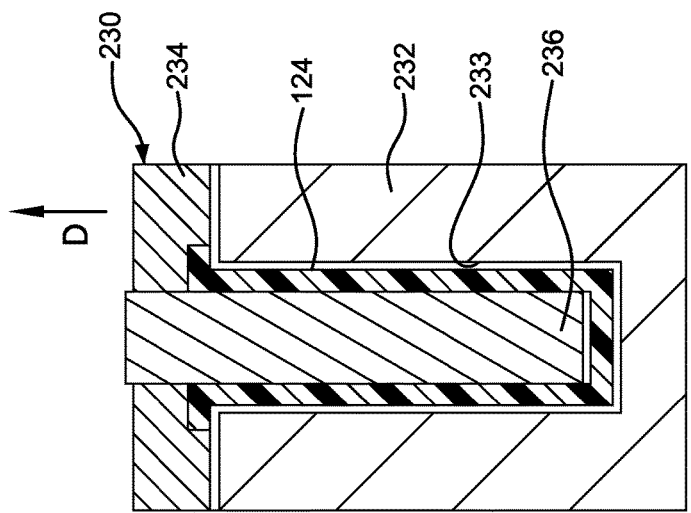
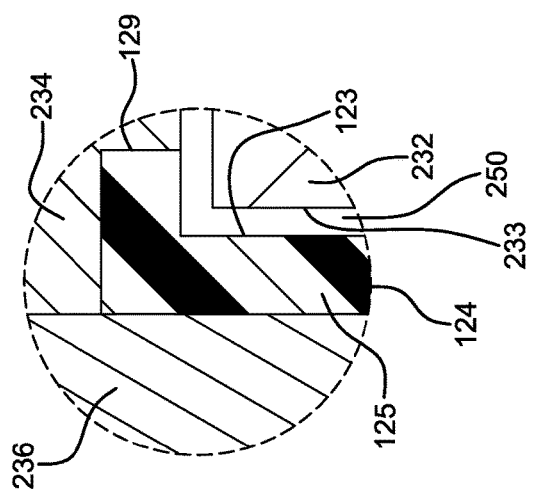
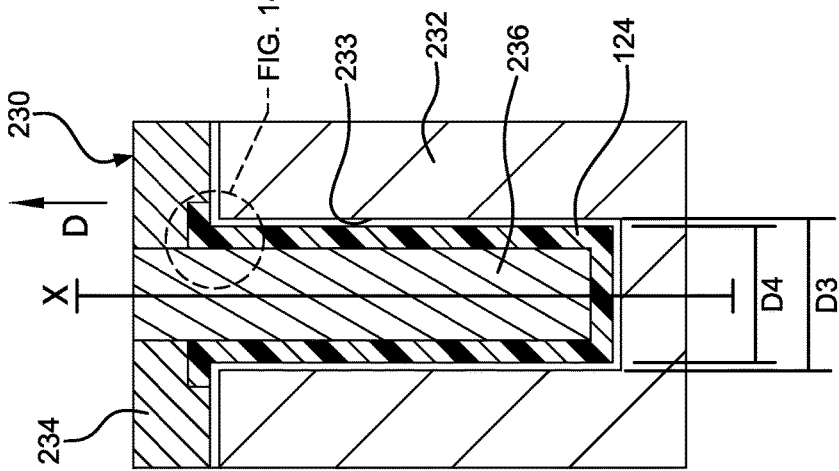

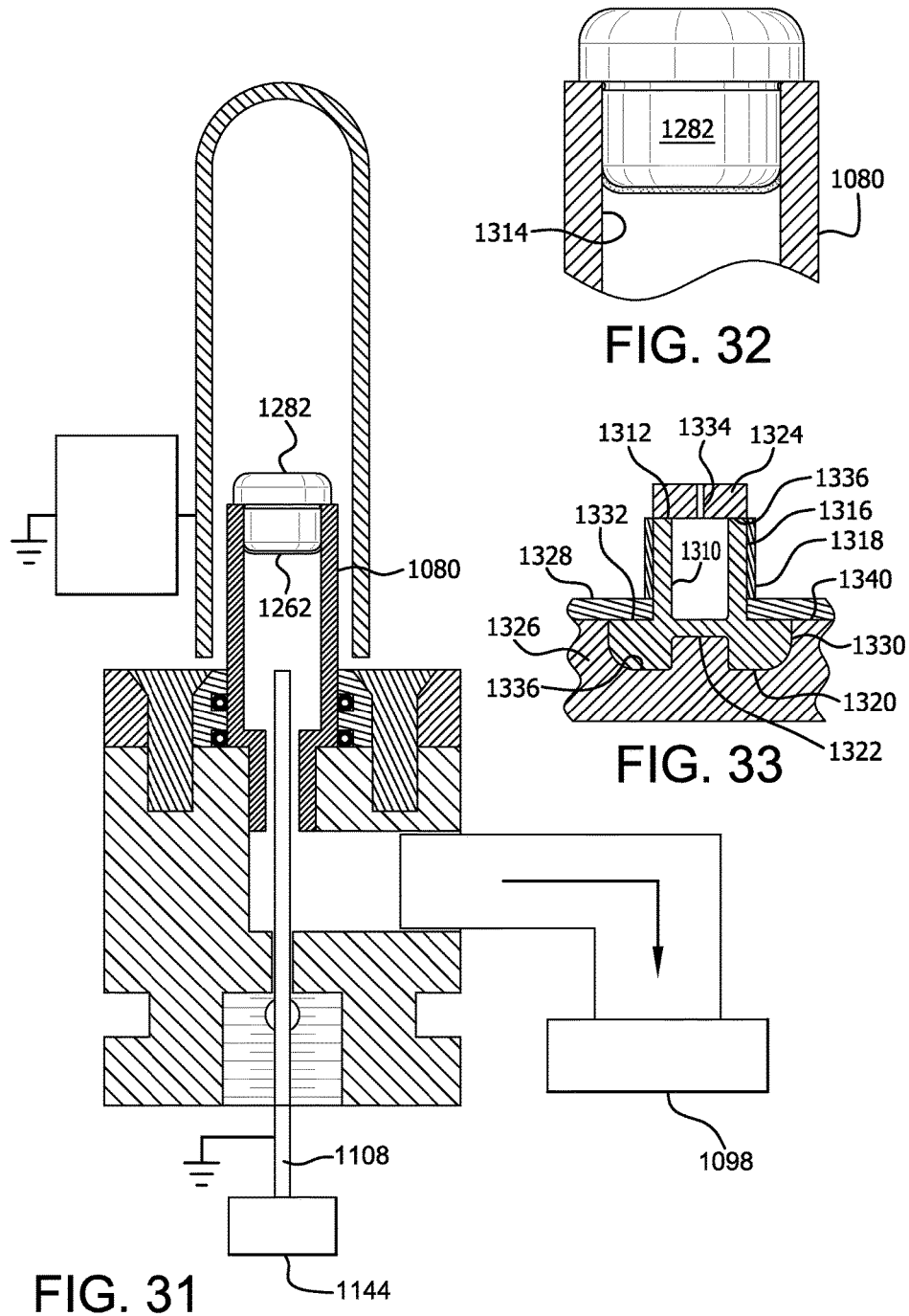

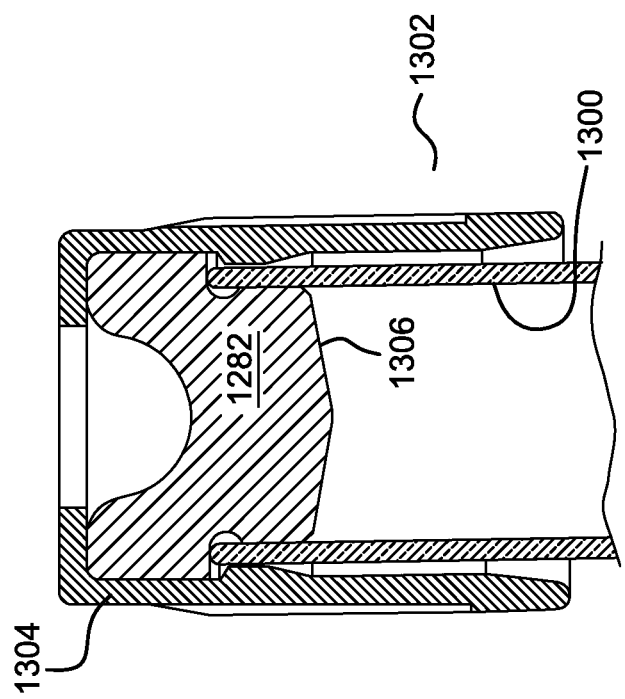
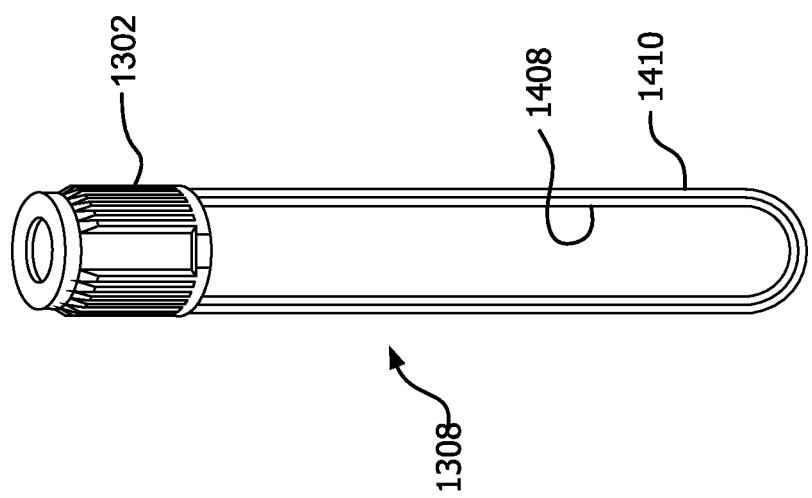

INJECTION MOLDING PROCESSES FOR MOLDING BARREL AND THERMOPLASTIC SYRINGES HAVING LOW AXIAL DRAFT ANGLES

CROSS-REFERENCE TO RELATED APPLICATIONS

This application is a Continuation Application of U.S. application Ser. No. 13/809,455 filed Jan. 10, 2013 which is a U.S. National Phase of International Application No. PCT/US2011/044215 filed Jul. 15, 2011, which claims priority to U.S. Provisional Patent Application Nos. 61/365,277 filed Jul. 16, 2010 and 61/413,329 filed Nov. 12, 2010, which are incorporated herein by reference in their entirety.

FIELD OF INVENTION

One aspect of the invention pertains to a molding method, and in particular a molding method employing a mold portion formed of a material having a selected coefficient of thermal expansion. Another aspect of the invention pertains to a product produced in accordance with such a molding method.

BACKGROUND

Injection molded devices having hollow interior portions or defining interior spaces are often formed using molding equipment having a hollow outer portion and an inner core portion. A molding space between the outer portion, inner core, and possible additional mold portions is injected with a molding material, such as a heated thermoplastic material. The molding equipment, and in turn the molding material, is then cooled to a temperature below the glass transition temperature of the molding material and the finished product formed from the molding material is removed from the molding space. The molding space is typically formed with draft angles to permit removal of the inner core portion from the finished product and/or removal of the finished product from the hollow outer portion. Examples of devices formed in this manner would be syringe barrels and plungers, which typically have generally cylindrical bodies defining interior regions. The interior region and outer surface of the cylindrical body are formed with draft angles, such these surfaces are not parallel to a central axis of the body, but are instead slightly angled with respect thereto to form a generally conical shape.

A stage of a molding operation of a plastic syringe barrel 12 having this configuration is shown in FIG. 1A. As shown, the outer surface 48 of the mold inner core 36 and inner surfaces 33, 35 of lower plate 32 and upper plate 34 are disposed at a draft angle θ (theta) with respect to central axis x of the molding equipment 30. This permits withdrawal of inner core 36 in direction D from the interior of the finished syringe barrel 12 without interference between the inner surface 15 of syringe barrel body 14 and outer surface 48 of inner core 36. FIG. 1A shows the assembly during withdrawal of the inner core 36 from the syringe barrel 12. It should be noted that for illustrative purposes the angle θ is somewhat exaggerated in FIG. 1A with respect to that of a typical syringe barrel.

A stage of a molding operation of a plastic syringe plunger 124 is shown in FIG. 1B. As shown, the outer surface 348 of the mold inner core 54 and inner surfaces 51, 53 of lower plate 50 and upper plate 52 are disposed at a draft angle φ (phi) with respect to central axis x of the molding equipment 49. This permits withdrawal of the molded syringe plunger 124 in direction D from the molding space 55 defined in lower plate 50 without interference between the outer surface 323 of plunger body 125 and inner surface 51 of lower plate 50. FIG. 1B shows the assembly during withdrawal of the plunger 324 from the molding space 55. It should be noted that for illustrative purposes the angle φ is somewhat exaggerated in FIG. 1B with respect to that of a typical syringe plunger.

After the syringe barrels such as 12, or any other syringe barrels or other vessels described herein, are molded, it is frequently desirable to provide them with an SiOx barrier layer and/or an $Si_wO_xC_y$ lubricity or hydrophobicity or other surface property modifying layer as extensively explained, for example, in U.S. Publ. Appl. No. 2010/0298738 A1, published Nov. 25, 2010, issued as U.S. Pat. No. 7,985,188 on Jul. 26, 2011. The latter publication and patent are incorporated here by reference to show suitable barrier, lubricity, and surface modifying layers and how they can be applied.

After molding, a finished product is assembled including a syringe plunger used to force a liquid dosage out of the syringe for administration into a patient. The plunger is slidably disposed within cylindrical body of the barrel. The plunger ideally has approximately the same outer diameter as the inner diameter of the syringe barrel, in order to permit slidable engagement therewith while preventing leakage of the liquid dosage from gaps between the plunger and barrel. The draft angles of typical plastic syringe barrels and plungers, typically about 1° to 3° can create difficulty in this respect, as they cause variations in the inner diameter of the barrel and/or plunger. Several measures can be taken to compensate for this. For example, the plunger may be formed of an elastomeric material that permits deformation thereof during sliding within the barrel cylindrical body. The outer diameter of the elastomeric plunger is large enough to compensate for the variation in the inside diameter of the syringe barrel. The oversized plunger creates interference with the syringe barrel that requires higher force to move plunger within the syringe barrel. One measure taken to address the higher plunger force required with a syringe having an elastomeric plunger the application of a lubricity layer, such as silicon oil applied to the interior of the syringe barrel and/or the plunger to lubricate and facilitate sliding of the plunger within the barrel. FIGS. 10A through 10G illustrate one of the problems with syringes employing this type of lubricity layer. As shown, the layer material, which is silicon oil in the example of FIGS. 10A through 10G, can be displaced by the plunger. Over time and/or due to sliding of the plunger, portions of the silicon oil typically migrate, leading to nonuniformity of the layer. This can make subsequent sliding of the plunger more difficult. Further, some of the lubricity material can expelled from the syringe along with the dosage, and in some cases injected into a patient receiving the dosage. For this reason, plastic molded syringes are often intended to be used only once and disposed of.

Another problem caused by the inclusion of draft angles within a plastic syringe barrel and/or plunger is that of nonuniformity of the pressure required to be applied to the barrel during dosage administration. Due to the decreasing inner diameter of the barrel wall and/or the increasing outer diameter of the plunger wall, the amount of pressure applied must be increased as the plunger approaches the needle end of the syringe. This can cause stalling during administration, which can result in pain to the patient receiving the dosage. Additionally, this may cause difficulty in administering a dosage using an auto injector, i.e., a mechanical device that administers a dosage using, for example, a spring loaded mechanism or motor, as these devices may not be able to perceive a change in resistance as readily as a human administrator.

Other prior patents in this area are U.S. Pat. Nos. 5,141, 430; 5,022,563; and 5,971,722.

Glass syringes and other vessels have traditionally been favored over thermoplastic syringes and vessels because glass is more gas tight and inert to pre-filled contents than untreated plastics. Also, due to its traditional use, glass is well accepted, as it is known to be relatively innocuous when contacted with medical samples or pharmaceutical preparations and the like. Glass syringes are also fabricated from extruded tubing, which does not require a draft angle. But it is desirable for certain applications to move away from glass vessels, which can break and are expensive to manufacture, in favor of plastic vessels which are rarely broken in normal use (and if broken do not form sharp shards from remnants of the vessel, like a glass tube would) and inexpensive to manufacture by injection molding in a multi-use mold. A need exists for a plastic syringe that can be formed by injection molding in a multi-use mold free or partially free of draft angles, in order to eliminate the problems discussed above.

SUMMARY

One aspect of the invention is a method of molding a solid article.

Multiple-use injection molding equipment is provided, including a substantially rigid surface defining a cavity and a substantially rigid core. The cavity and core define a molding space between them. At least one of the cavity and the core is movable with respect to the other along a parting axis to open the molding space for removing molded articles. At least one portion of the cavity or the core is a low draft element. A low draft element is defined in this specification as an element having a draft angle of 0.5 degree or less xxx with respect to the parting axis. A draft angle of 0.5 degree or less with respect to the parting axis is defined in this specification as low draft.

The method includes a step of heating at least part of the low draft element to a first selected temperature to expand it. Before, during or after heating, a fluid molding material is injected into the molding space. At least a surface of the fluid molding material is formed against the low draft element to define a low draft formed surface. At least the low draft formed surface is solidified to provide a solid low draft formed surface.

The method includes a step of cooling at least part of the low draft element to a second selected average temperature less than the first selected temperature. Sufficient cooling is carried out to thermally contract at least a portion of the low draft element away from the solid low draft formed surface sufficiently to release the low draft element from the low draft formed surface. The method is continued by parting the cavity and core along the parting axis and removing the solid article from the molding space. Another aspect of the invention is a syringe assembly made by the method above.

Still another aspect of the invention is a syringe assembly including a barrel and a piston. The barrel includes a generally cylindrical side wall. The side wall is made of substantially rigid thermoplastic material defining a bore for containing a liquid. The bore has an axial draft angle of 0 to 0.5 degrees, optionally at least substantially zero degrees. The piston has a leading face, a trailing face, and a side edge configured to movably seat in the bore. The side edge is made of substantially rigid thermoplastic material.

Even another aspect of the invention is a method for selectively coating a syringe plunger or similar article using plasma enhanced chemical vapor deposition, the method is carried out as follows.

A syringe plunger is provided having a generally circular front portion positioned for contacting contents of a syringe barrel and a generally cylindrical side portion adapted for slidably contacting a syringe barrel. A generally tubular plunger holder is provided having a front opening and an inner sidewall extending from the front opening.

The plunger is placed in the plunger holder, oriented with the front portion of the plunger facing the front opening of the plunger holder and the side portion of the plunger contacting the inner sidewall of the plunger holder. The front portion of the plunger is contacted with a layer forming reactive gas, and a plasma is formed in the plunger holder adjacent to the front portion of the plunger. The result is to deposit a barrier layer selectively on the front portion of the plunger, using plasma enhanced chemical vapor deposition.

Still another aspect of the invention is another method for selectively coating a syringe plunger.

A syringe plunger is provided having a generally circular front portion positioned for contacting contents of a syringe barrel; a generally cylindrical side portion adapted for slidably contacting a syringe barrel, and a generally circular back portion. The syringe plunger is placed in a plasma enhanced chemical vapor deposition chamber. At least one of the generally circular front portion and the generally circular back portion is masked. This is done at least substantially without masking at least a portion of the generally cylindrical side portion of the plunger. The side portion of the plunger is contacted with a layer forming reactive gas. Plasma is formed in the deposition chamber adjacent to the side portion of the plunger. As a result, a layer is selectively formed on the side portion of the plunger using plasma enhanced chemical vapor deposition.

Additional aspects of the invention will be apparent from the following description of the invention and the appended claims.

BRIEF DESCRIPTION OF THE DRAWING FIGURES

FIGS. 10A and 10B are schematic illustrations showing initial placement of a plunger in a typical syringe barrel having a silicon oil lubricity layer disposed on the barrel wall;

FIGS. 10C through 10E are schematic illustrations showing that the silicon oil layer on the barrel of FIGS. 10A and 10B can be forced out from the area between the plunger and the syringe wall over time;

FIGS. 10F and 10G are schematic illustrations showing migration and nonuniformity of the silicon oil layer on the barrel of FIGS. 10A and 10B over time.

FIG. 14 is a cross sectional view showing a third stage of a molding operation of a syringe plunger in accordance with the present invention;

FIG. 14A is an enlarged detail, showing the a clearance space between the syringe plunger and the mold lower plate of FIG. 14;

FIG. 15 is a cross sectional view showing a release stage of the molding operation of FIGS. 12-14;

FIG. 31 is a is a longitudinal section of alternative apparatus for forming a layer on the end of a generally cylindrical object, here a stopper;

FIG. 32 is an enlarged detail view of the stopper shown in FIG. 6, illustrating its parts;

FIG. 33 is a schematic sectional detail view of a septum, showing masks to confine a layer to the side of the stopper;

FIG. 34 shows a perspective view of an evacuated blood collection tube and closure assembly;

FIG. 35 is a fragmentary longitudinal section of FIG. 9, showing the stopper and shield assembly seated on a tube, which can be a vessel neck, as shown in FIG. 9, or a holder for layer the stopper while it is assembled with the shield.

The following reference numbers are used in the specification. Like numbered parts in the respective views show corresponding elements.

Figure 1A:
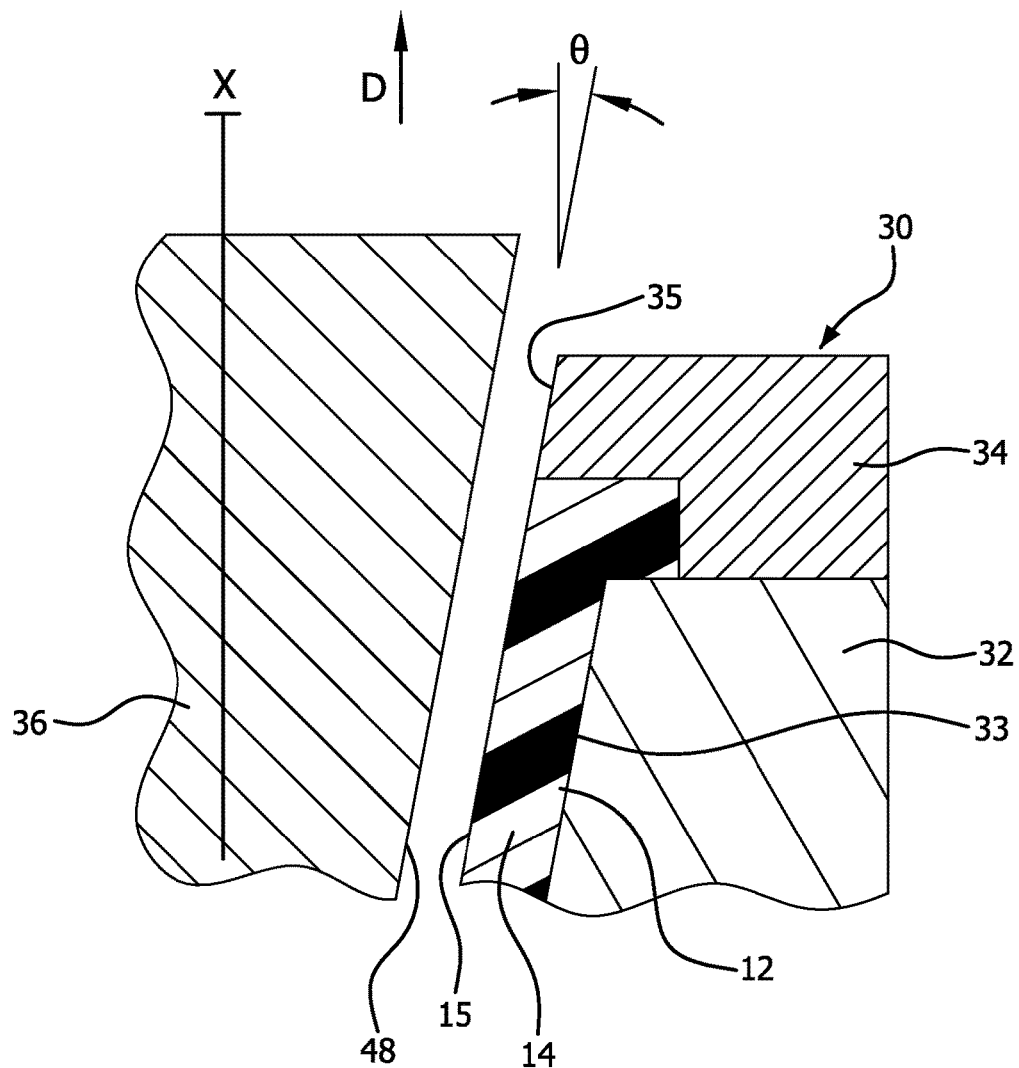
FIG. 1A is an enlarged detail of a cross sectional view showing a stage of a prior art molding operation of a syringe barrel.

| Reference Number List | |
|---|---|
| 10 | Syringe |
| 12 | Barrel |
| 14 | Cylindrical Body |
| 15 | Inner Surface (of 14) |
| 30 | Mold |
| 32 | Lower Plate |
| 33 | Inner Surface (of 32) |
| 34 | Upper Plate |
| 35 | Inner Surface (of 34) |
| 36 | Inner Core |
| 48 | Outer Surface (of 36) |
| 49 | Mold |
| 50 | Lower Plate |
| 51 | Inner Surface (of 50) |
| 52 | Upper Plate |
| 53 | Inner Surface (of 52) |
| 54 | Inner Core |
| 55 | Molding Space |
| 110 | Syringe |
| 112 | Barrel |
| 114 | Cylindrical Body (of 112) |
| 115 | Inner Surface (of 114) |
| 116 | Interior of (112) |
| 118 | Barrel Hub |
| 120 | Needle |
| 122 | Needle Hub |
| 124 | Plunger |
| 126 | Open End (of 112) |
| 128 | Collar |
| 130 | Mold |
| 132 | Lower Plate |
| 133 | Inner Surface (of 132) |
| 134 | Upper Plate |
| 135 | Inner Surface (of 134) |
| 136 | Inner Core |
| 138 | Molding Cavity |
| 140 | Opening (of 134) |
| 142 | Groove (of 134) |
| 144 | Molding Space |
| 146 | Molding Material |
| 148 | Outer Surface (of 136) |
| 150 | Clearance |
| 152 | Bottom Portion (of 144) |
| 160 | Outer Expansion Layer (of 136) |
| 162 | Conduction Layer (of 136) |
| 164 | Inner Layer (of 136) |
| 166 | Cooling Channel (of 136) |
| 170 | Seal |
| 172 | Depressor |

-continued

| Reference Number List | |
|---|---|
| 174 | Collar |
| 210 | Test Tube |
| 214 | Cylindrical Body (of 210) |
| 216 | Interior (of 214) |
| 230 | Mold |
| 232 | Lower Plate |
| 234 | Upper Plate |
| 236 | Inner Core |
| 238 | Molding Cavity |
| 240 | Opening (of 234) |
| 242 | Groove (of 234) |
| 244 | Molding Space |
| 246 | Molding Material |
| 252 | Closed Bottom (of 244) |
| 310 | Syringe assembly |
| 312 | Barrel |
| 314 | Side wall (of 312) |
| 316 | Bore (of 312) |
| 318 | Piston |
| 320 | Leading face (of 318) |
| 322 | Trailing face (of 318) |
| 324 | Side edge (of 318) |
| 326 | Lubricant |
| 328 | Stem |
| 330 | First end portion (of 328) |
| 332 | Second end portion (of 328) |
| 334 | Tubular section (of 28) |
| 336 | Generally cross-shaped section (of 328) |
| 338 | Rod section (of 328) |
| 340 | Open end (of 334) |
| 342 | Closed end (of 334) |
| 344 | Dispensing opening (of 312) |
| 346 | Hypodermic needle |
| 423 | Outer Surface (of 425) |
| 423A | First Portion (of 423) |
| 423B | Second Portion (of 423) |
| 424 | Plunger |
| 425 | Body (of 424) |
| 430 | Mold |
| 432 | Lower Plate |
| 433 | Inner Surface (of 432) |
| 434 | Upper Plate |
| 436 | Inner Core |
| 437 | Middle Plate |
| 437A | First Portion (of 437) |
| 437B | Second Portion (of 437) |
| 523 | Outer Surface (of 525) |
| 523A | First Portion (of 523) |
| 523B | Second Portion (of 523) |
| 524 | Plunger |
| 525 | Cylindrical Body (of 524) |
| 530 | Mold |
| 532 | Lower Plate |
| 533 | Inner Surface (of 532) |
| 534 | Upper Plate |
| 535 | Inner Surface (of 534) |
| 536 | Inner Core |
| 610 | Test Tube |
| 614 | Cylindrical Body (of 610) |
| 616 | Interior (of 610) |
| 630 | Mold |
| 632 | Lower Plate |
| 634 | Upper Plate |
| 644 | Molding Space |
| 652 | Closed Bottom (of 616) |
| 1028 | Layer station |
| 1050 | Vessel holder |
| 1080 | Plunger holder |
| 1082 | Opening |
| 1086 | Wall |
| 1088 | Inner sidewall (of 1080) |
| 1098 | Vacuum source |
| 1104 | Gas inlet port |
| 1108 | Probe (counter electrode) |
| 1110 | Gas delivery port (of 1108) |
| 1118 | Exterior surface (of 80) |
| 1144 | PECVD gas source |
| 1160 | Electrode |
| 1162 | Power supply |
| 1164 | Sidewall (of 160) |
| 1166 | Sidewall (of 160) |
| 1250 | Syringe barrel |
| 1252 | Syringe |
| 1254 | Interior surface (of 250) |
| 1256 | Open end (of 250) |
| 1258 | Plunger (of 252), example of generally cylindrical article |
| 1260 | Front end (of 250) |
| 1262 | Generally circular front portion or end portion (of 258) |
| 1264 | Contents (of 250) |
| 1266 | Generally cylindrical side portion (of 258) |
| 1268 | Generally circular back portion |
| 1270 | Plunger push rod |
| 1272 | Thumb pad (of 270) |
| 1274 | Piston ring |
| 1276 | Piston ring |
| 1278 | Chamfer |
| 1280 | Barrier layer |
| 1282 | Stopper |
| 1290 | Deposition chamber |
| 1292 | Mask |
| 1294 | Seat |
| 1296 | Layer |
| 1298 | First opening (of 80) |
| 1300 | Bore |
| 1302 | Vessel closure (stopper and shield assembly) |
| 1304 | Shield (of 302) |
| 1306 | Stopper end portion |
| 1308 | vessel |
| 1310 | septum |
| 1312 | Central end portion (of 310) |
| 1314 | Second opening (of 300) |
| 1316 | Side portion (of 310) |
| 1318 | Layer |
| 1320 | End portion (of 310) |
| 1322 | Web (of 310) |
| 1324 | Mask |
| 1326 | Mask |
| 1328 | Mask |
| 1330 | Side portion (of 310) |
| 1332 | Peripheral end portion (of 310) |
| 1334 | Vent passage |
| 1336 | Mating portion |
| 1338 | Mating portion |
| 1340 | Surface |
| 1408 | Vessel interior wall or surface |
| 1410 | Vessel exterior wall |

DETAILED DESCRIPTION OF THE PREFERRED EMBODIMENT(S)

Certain terminology is used in the foregoing description for convenience and is not intended to be limiting. Words such as "front," "back," "top," and "bottom" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 2:
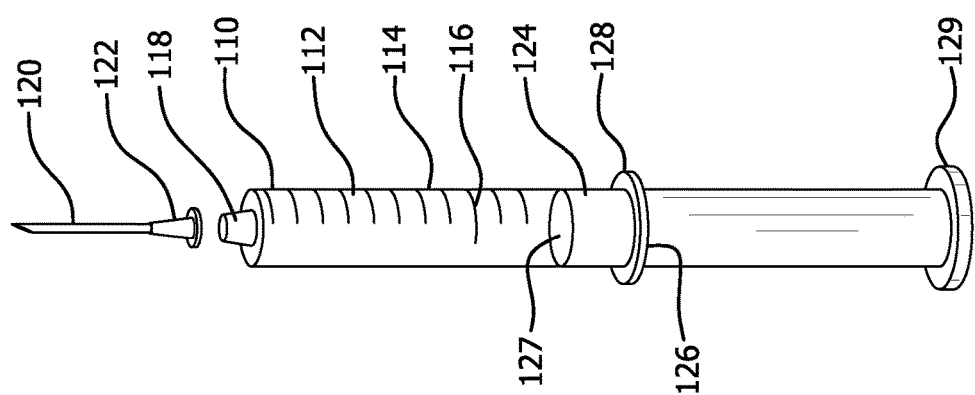
FIG. 2 is a perspective view of an exemplary syringe having a barrel and a plunger molded in accordance with the invention.

FIG. 2 shows an example of a molded syringe 110. As shown, the syringe 110 includes a barrel 112 having a substantially cylindrical shaped body 114 defining an interior 116 for housing an injectable medication. A barrel hub 118 extends from the top of the barrel 112 for attachment of a needle 120. The needle 120 includes a needle hub 122 that engages the barrel hub 118. A collar 128 extends radially outward from the barrel 112 about the open end 126, for gripping by a user when injecting a medication using the syringe 110. A plunger 124 is slidably disposed within the interior 116 of the barrel 114 and protrudes from open end 126 thereof. The plunger 124 includes a cylindrical shaped body 125 a base 127 that closes off one end of the cylindrical body 125 and a collar 129 that extends radially outward from the cylindrical body 125 at the end opposite the base 127.

Figure 3:
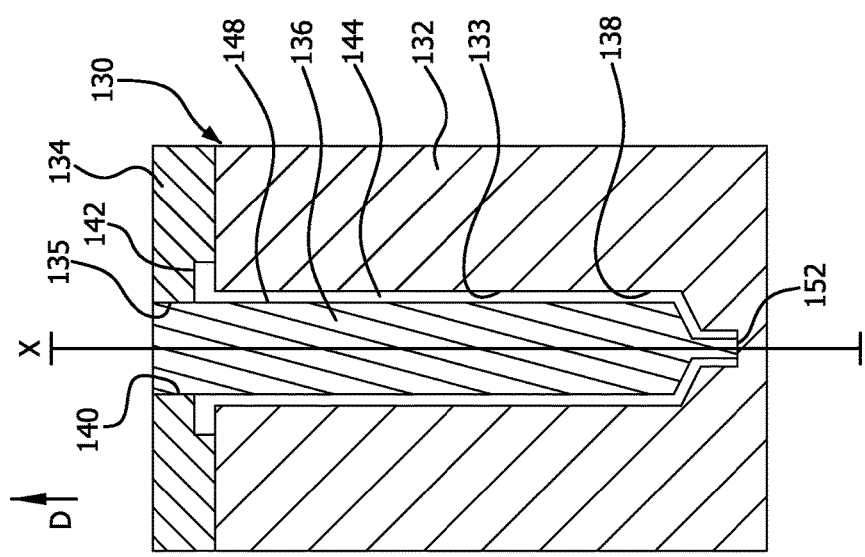
FIG. 3 is a cross sectional view showing a first stage of a molding operation of a syringe barrel in accordance with the present invention.

One aspect of the present invention is directed to a method of molding a product substantially or entirely free of draft angles on an interior surface thereof, such as a syringe barrel 112. FIGS. 3-6 show one embodiment of a molding operation for molding the syringe barrel 112 of FIG. 2. Referring first to FIG. 3, a mold 130 in accordance of the invention is shown. As shown, the mold 130 includes a lower plate 132, an upper plate 134, and an inner core 136. The lower plate 132 defines a molding cavity 138 shaped to define outer surfaces of the cylindrical body 114 and the barrel hub 118. The inner core 136 is sized and shaped to fit within the molding cavity 138 and define inner surfaces of the cylindrical body 114 and barrel hub 118. The upper plate 134 sits above the lower plate 132 and includes an opening 140 that receives the inner core 136. A circumferential groove 142 about the opening 140 of the upper plate 134 is shaped to define the collar 128. As shown, the lower plate 132, upper plate 134 and inner core 136, when assembled in the configuration shown in FIG. 3, together define a molding space 144 therebetween for receiving a molding material 146. The molding space 144 substantially has the shape of the desired syringe barrel 112 to be produced using the mold 130.

Referring still to FIG. 3, a first stage of a molding operation in accordance with the invention is shown. The lower plate 132, upper plate 134, and inner core 136 are assembled to define the molding space 144 in the shape of the desired syringe barrel 112. The inner core 136, and optionally the lower plate 132 and upper plate 134, are heated before introducing molding material 146 into the molding space 144. Time during which the inner core 136 and optionally the lower plate 132 and upper plate 134 are heated may be minimized, so as to minimize energy costs and stress on the materials forming these portions of the mold, which could lead to material fatigue. In the configuration shown in FIG. 3, the only substantial clearances between the lower plate 132, upper plate 134, and inner core 136 are those defining the molding space 144. The inner core 136, lower plate 132, and upper plate 134 can each be heated by any means known in the art. For example these elements may be heated by induction using a heating coil, as in US 2009/0239023, which is incorporated by reference herein as if fully set forth.

The outer surface 148 of the inner core 136 is of a cylindrical shape in FIG. 3. As such, the outer surface 148 is parallel to the central axis x of the molding space 144. Accordingly, there are substantially no draft angles to facilitate extraction of the inner core 136. In contrast, a typical mold for a syringe barrel 112 would have a slightly conical shape, rather than cylindrical, with diameter increasing approaching the top of the inner core 136 and decreasing towards the bottom. FIG. 1A shows an enlarged detail of a typical molding arrangement in which the barrel wall is disposed at an angle θ with respect to a central axis x of the syringe barrel 112.

The inner core 136 is preferably at least partially formed of a material or materials having a selected coefficient of thermal expansion to permit ejection of the finished syringe barrel 112 without the need for a draft angle (θ) greater than zero, as described in detail below.

Figure 11:
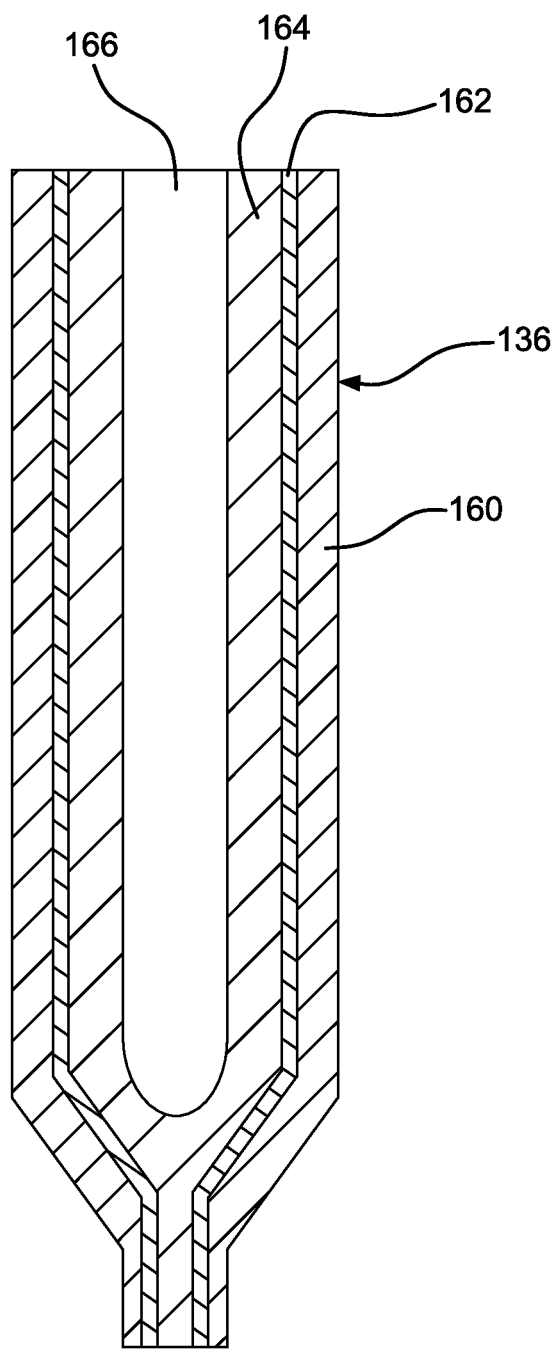
FIG. 11 is a cross sectional view showing an inner core of one embodiment of the present invention for molding a syringe barrel.

FIG. 11 illustrates one embodiment of an inner core 136 for molding a syringe barrel 112 according to the method described above. As shown, the inner core 136 includes an outer expansion layer 160, a conduction layer 162, an inner layer 164 and a central cooling channel 166. The outer expansion 160 layer is formed of a material selected based on its thermal expansion properties. In one embodiment, the outer expansion layer 160 is formed of steel, such as an H13 tool grade steel. Different materials could be used as well, depending upon the thickness of the outer expansion layer 160, the desired clearance 150, and the coefficient of thermal expansion of the potential material. The conduction layer 162 is located inward with respect to the outer expansion layer 160 and is formed of a material selected based upon its conductive properties. In one embodiment, the conduction layer 162 is formed of copper. Specific types of copper or other materials could be selected depending upon the thickness of the conductive layer 162, the desired clearance 150, and the conductivity of the potential material. The inner layer 164 is located inward of the conduction layer 162 and may be formed of the same material as the outer expansion layer 160, or another material capable of withstanding the heating and cooling cycles of the inner core 136. The central cooling channel 166 is located inward of the inner layer 164 along a central portion of the inner core 136. The central cooling channel 166 can be configured to receive a refrigerant for cooling the molding core. Any suitable configuration known in the art can be employed for the cooling channel, such as that disclosed by U.S. Pat. No. 5,573,787 or U.S. Pat. No. 7,303,387, which are incorporated herein by reference as if fully set forth.

The inner core 136 is sized so that when heated to a selected molding temperature, it expands to a size whereby the outer surface(s) 148 thereof has the desired dimensions of the inner surface(s) 115 of the cylindrical body 114 and hub 118 of the syringe barrel 112.

Figure 4:
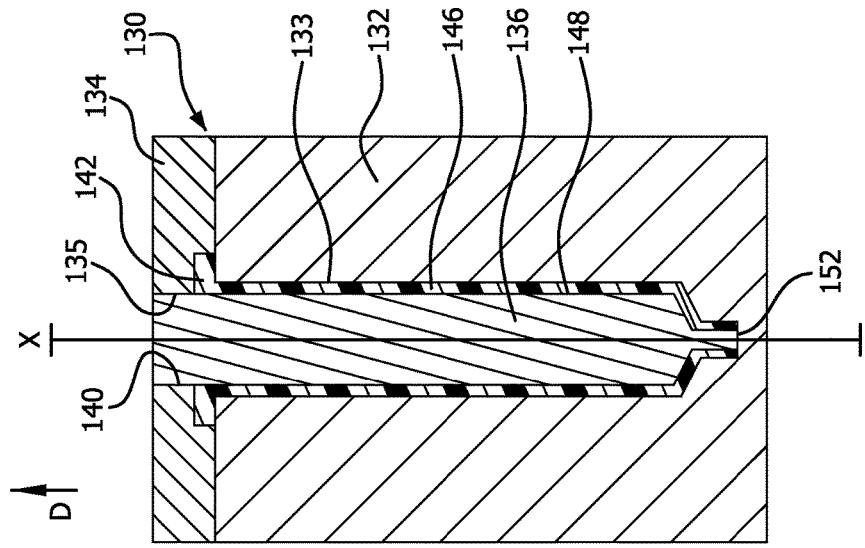
FIG. 4 is a cross sectional view showing a second stage of a molding operation of a syringe barrel in accordance with the present invention.

In FIG. 4, the molding material 146 has been introduced into the molding space 144. The molding material 146 is preferably a thermoplastic polymeric material, such as cyclic olefin copolymer (COC), polyethylene terephthalate (PET), or polypropylene (PP). The molding material 146 is heated above its melting point and flows to completely fill the molding space 144. Heat may be provided by way of the heated inner core 136 and optionally heated lower plate 132 and/or upper plate 134. Optionally, additional heat sources may be used as well. In one preferred embodiment using COC or PP as the molding material 146, the inner core 136 molding temperature is between 160° C. and 210° C. The lower plate 132 and/or upper plate 134 may optionally be heated to this temperature as well. Alternatively, these portions could be heated to different temperatures. In one embodiment, the molding temperature(s) that the inner core 136 and optionally lower plate 132 and/or upper plate 134 are selected to control flow of the molding material 146. In another embodiment, the core 136 is heated to the minimum temperature needed to eliminate any clearances between it and the upper plate 134 and lower plate 132, so as to minimize fatigue of the material caused by repeatedly heating and cooling during molding operations.

Figure 5A:
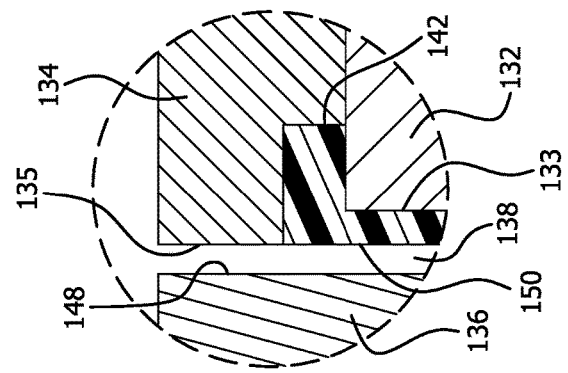
FIG. 5A is an enlarged detail, showing a clearance formed between the syringe barrel and the mold core of FIG. 5.
Figure 5:
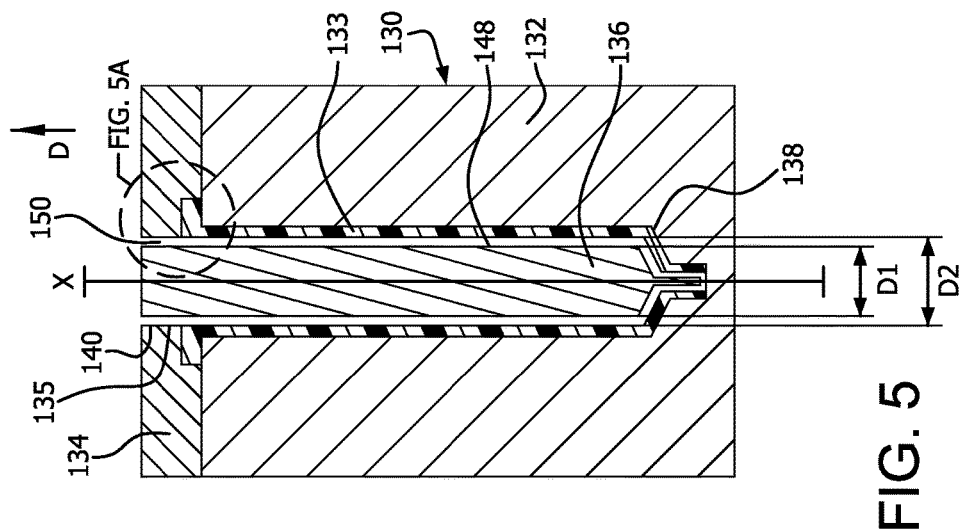
FIG. 5 is a cross sectional view showing a third stage of a molding operation of a syringe barrel in accordance with the present invention.

A subsequent stage of the molding operation is shown in FIG. 5. At this stage, the inner core 136 is cooled. This cooling causes shrinkage of the inner core 136, giving it an outside diameter D1 less than the inside diameter D2 of the cylindrical body 114 and opening 140 of the upper mold plate 34, which are preferably substantially equal (see FIG. 5). This, in turn, creates a clearance 150 between the inner mold core 136 and the inner surface 115 of the cylindrical body 114, as well as between the upper plate 134 opening 140 and inner core 136, as shown in detail in FIG. 5A. The inner core 136 is preferably cooled at least to a temperature so as to cause sufficient shrinkage to eliminate any potential interference between the inner core 136 and cylindrical body 114, or between the inner core 136 and the opening 140 of the upper plate 134, thus permitting extraction of the syringe barrel 114 therefrom. In one embodiment, the inner core 136 is cooled sufficiently to a temperature to create a clearance 150 of 10 μm. In another embodiment, the inner core 136 is cooled sufficiently to a temperature to create a clearance 150 of 15 μm. In other embodiments the inner core 136 could be cooled to a temperature to create a larger or smaller clearance, depending on factors such as the size of the mold 130, the type of molding material 146, and end product geometry. Optionally, the lower plate 132 and upper plate 134 may be cooled at the same time as the inner core 136. Also optionally, the cooling of the inner core 136 and possibly the lower plate 132 and upper plate 134 may be of a degree sufficient to cause cooling of the molding material 146 below the melting point or glass transition temperature ($T_g$) thereof. The molding material 146 is preferably cooled below the glass transition temperature thereof before extraction. In a preferred embodiment, entire the inner core 136 is cooled at a uniform rate to encourage uniform setting of the molding material 146. Likewise, the upper plate 134 and lower plate 132 may each be cooled at a uniform rate. In another preferred embodiment, the inner core 136, lower plate 132 and upper plate 134 are all cooled at the same uniform rate. Likewise, any combination of the inner core 134, lower plate 132 and upper plate 136, as well as any additional mold portions that may be included, can be cooled at a uniform rate. In another embodiment, the rate of cooling of any of the mold portions is utilized to control the rate at which the molding material 146 sets, in order to impart desired characteristics in the finished syringe barrel 112.

Figure 6:
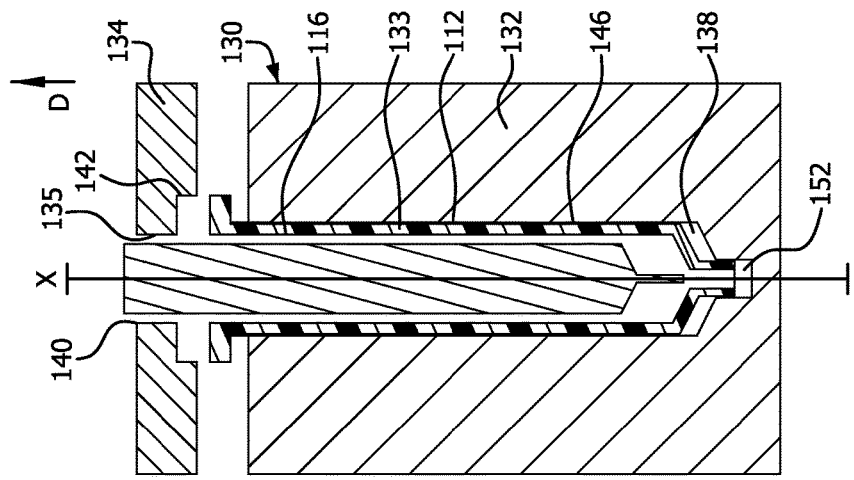
FIG. 6 is a cross sectional view showing a release stage of the molding operation of FIGS. 3-5.
Figure 7:
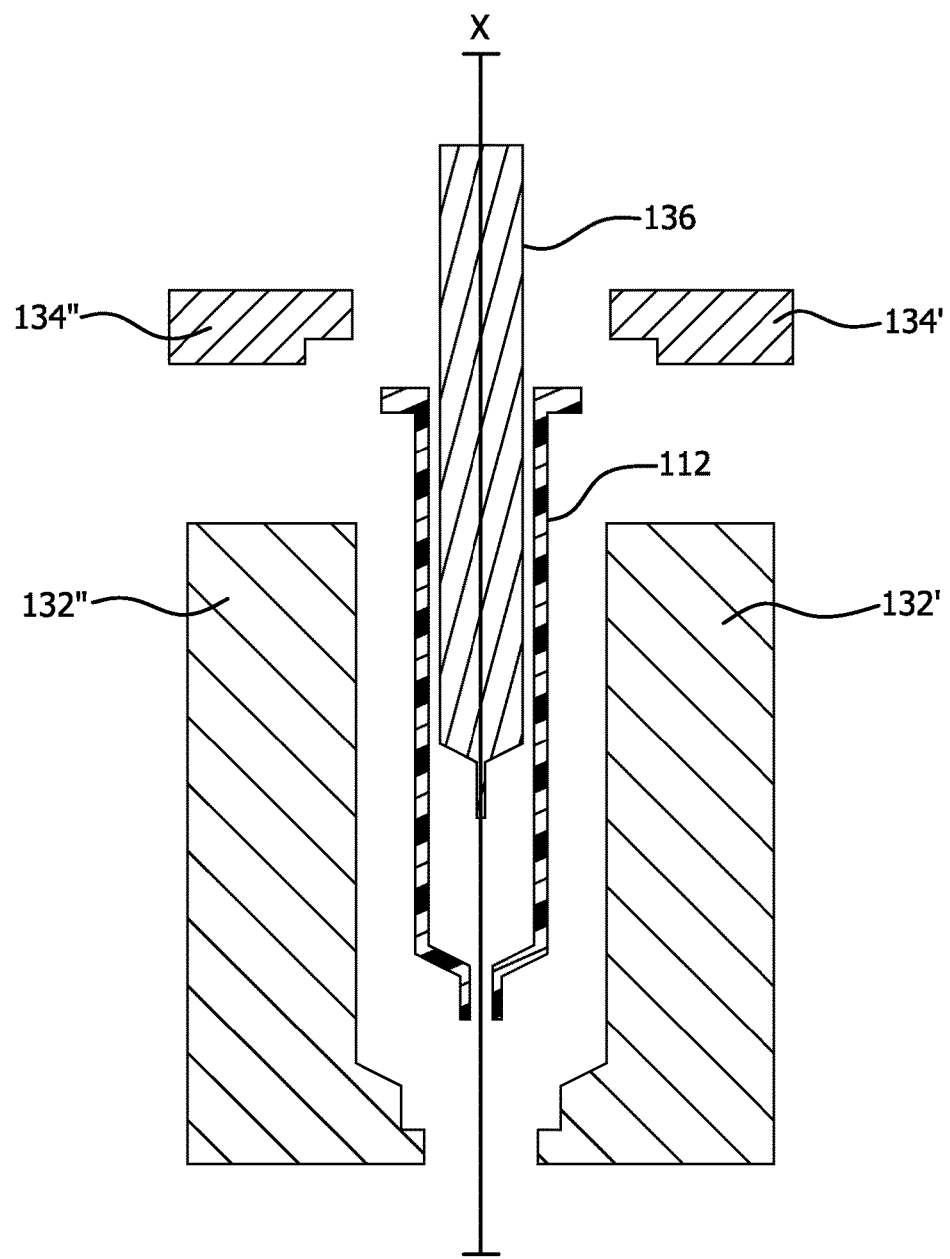
FIG. 7 is a cross sectional view showing a release stage of a molding operation of syringe barrel molded using a two part lower plate and a two part upper plate.

FIG. 6 shows an extraction stage of the molding operation. As shown, the molding material 146 is completely solidified to define the finished syringe barrel 112. The inner core 136 is easily extracted from the interior 116 of the cylindrical body 114 by moving it in direction D. The upper plate 134 is likewise removed from the lower plate 132 by moving it in direction D, and the barrel 112 can then be extracted from the mold cavity 138 of the lower plate 132 by moving it in direction D. In one embodiment, the mold cavity 138 and the opening 140 of the upper plate 134 are provided with draft angles (θ) to permit extraction of the syringe barrel 112 therefrom. Alternatively, the lower plate 132 and/or the upper plate 134 could be formed as multiple pieces. FIG. 7, shows the extraction stage of an alternative embodiment (side draw) in which the lower plate 132 and the upper plate 134 are each formed as two pieces 132A, 132B, 134A, 134B.

Figure 12:
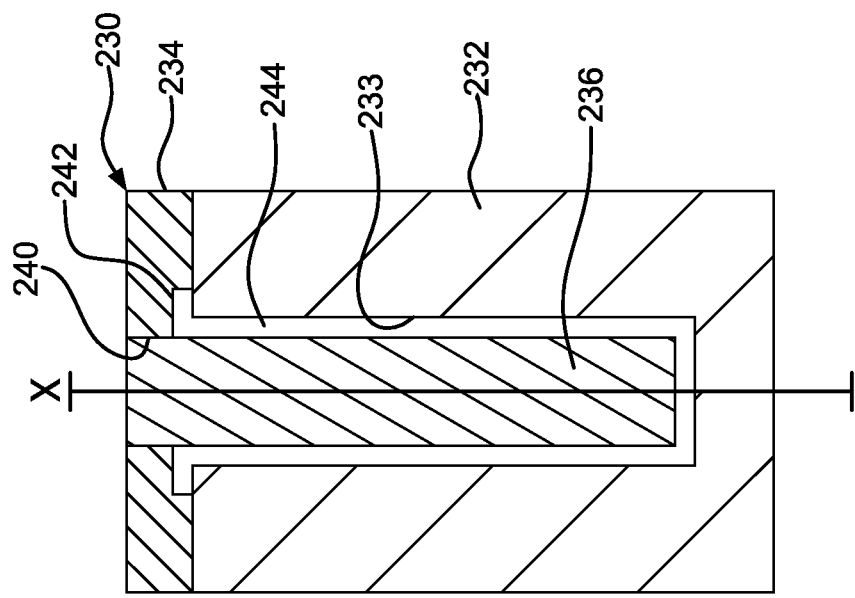
FIG. 12 is a cross sectional view showing a first stage of a molding operation of a syringe plunger in accordance with the present invention.

Another aspect of the present invention is directed to a method of molding a product substantially free of draft angles on an exterior surface thereof, such as a syringe plunger 124. FIGS. 12-15 show an embodiment of a molding operation for the syringe plunger 124 of FIG. 2. Referring first to FIG. 12, a mold 230 in accordance of the invention is shown. As shown, the mold 230 includes a lower plate 232, an upper plate 234, and an inner core 236. The lower plate 232 defines a molding cavity 238 shaped to define outer surfaces of the cylindrical body 125 and the base 127. The inner core 236 is sized and shaped to fit within the molding cavity 238 and define inner surfaces of the cylindrical body 125 and base 127. The upper plate 234 sits above the lower plate 232 and includes an opening 240 that receives the inner core 236. A circumferential groove 242 about the opening 240 of the upper plate 234 is shaped to define the collar 129. As shown, the lower plate 232, upper plate 234 and inner core 236, when assembled in the configuration shown in FIG. 12, together define a molding space 244 therebetween for receiving a molding material 246. The molding space 244 substantially has the shape of the desired syringe plunger 124 to be produced using the mold 230.

Referring still to FIG. 12, a first stage of a molding operation in accordance with the invention is shown. The lower plate 232, upper plate 234, and inner core 236 are assembled to define the molding space 244 in the shape of the desired syringe plunger 124. The lower plate 232 and optionally the inner core 236 and upper plate 234 are heated before introducing molding material 246 into the molding space 244. The time during which the lower plate 232 and optionally the inner core 236 and upper plate 234 are heated may be minimized, so as to minimize energy costs and stress on the materials forming these portions of the mold, which could lead to material fatigue. In the configuration shown in FIG. 12, the only substantial clearances between the lower plate 232, upper plate 234, and inner core 236 are those defining the molding space 244. The inner core 236, lower plate 232, and upper plate 234 can each be heated by any means known in the art. For example these elements may be heated by induction using a heating coil, as in US Publ. Appl. 2009/0239023, which is incorporated by reference herein as if fully set forth.

Figure 1B:
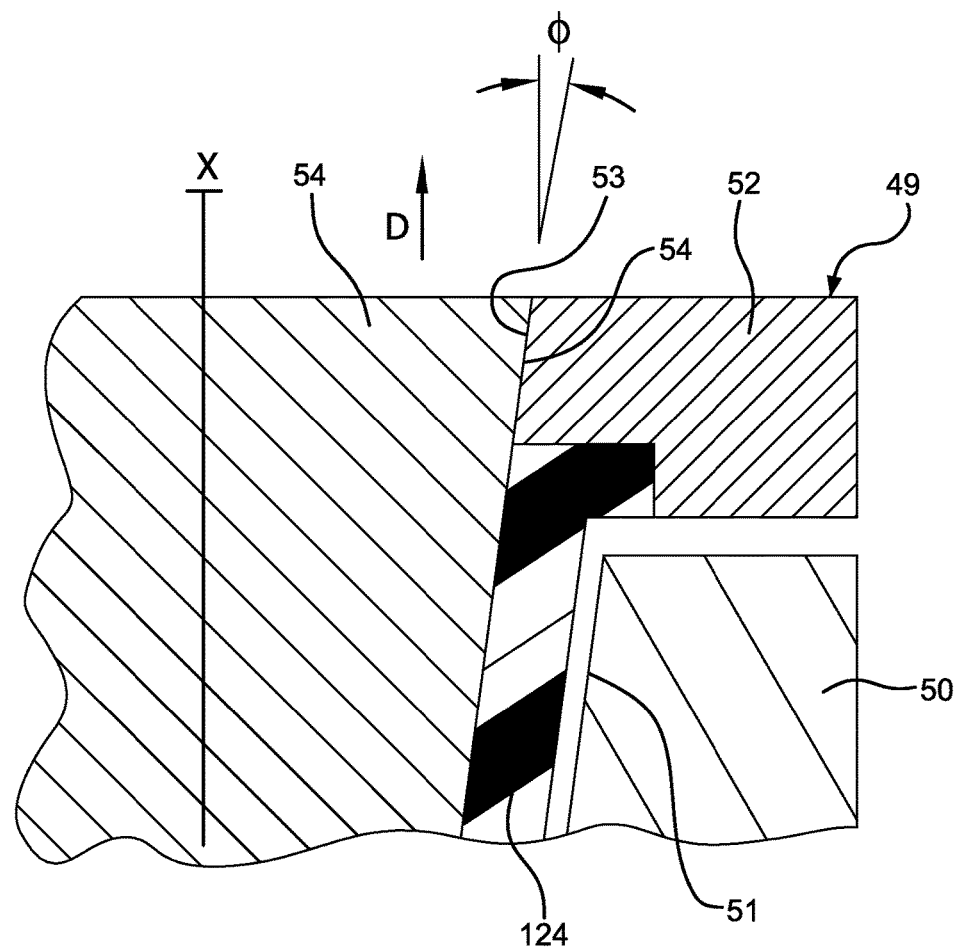
FIG. 1B is an enlarged detail of a cross sectional view showing a stage of a prior art molding operation of a syringe plunger.
Figure 8:
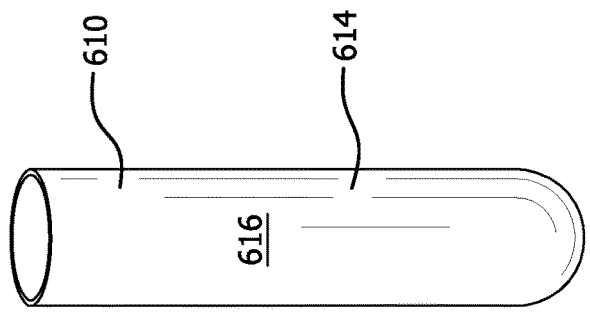
FIG. 8 is a perspective view showing an exemplary test tube molded in accordance with the present invention.

The inner surface 233 of the lower plate 232 is of a cylindrical shape in FIG. 12. As such, the inner surface 233 is parallel to the central axis x of the molding space 244. Accordingly, there are substantially no angles to facilitate extraction of the finished plunger 124 from the molding space 244. In contrast, the inner surface of an analogous lower plate for a typical mold for a syringe plunger of the type shown in FIG. 2 would have a slightly conical shape, rather than cylindrical, with diameter increasing approaching the top of the lower plate and decreasing towards the bottom. FIG. 1B shows an enlarged detail of a typical molding arrangement in which the plunger wall is disposed at an angle φ with respect to a central axis x of the plunger 124.

The lower plate 232 is preferably at least partially formed of a material or materials having a selected coefficient of thermal expansion to permit ejection of the finished plunger 124 without the need for draft angles, as described in detail below. For example the lower plate 232 could be formed or partially formed of steel, such as H13 tool grade steel. The lower plate 232 could further include a material selected based upon its conductive properties, such as copper.

The lower plate 232 is sized so that when heated to a selected molding temperature, it expands to a size whereby the inner surface(s) 233 thereof has the desired dimensions of the outer surface(s) 223 of the cylindrical body 125 and base 127 of the plunger 124.

Figure 13:
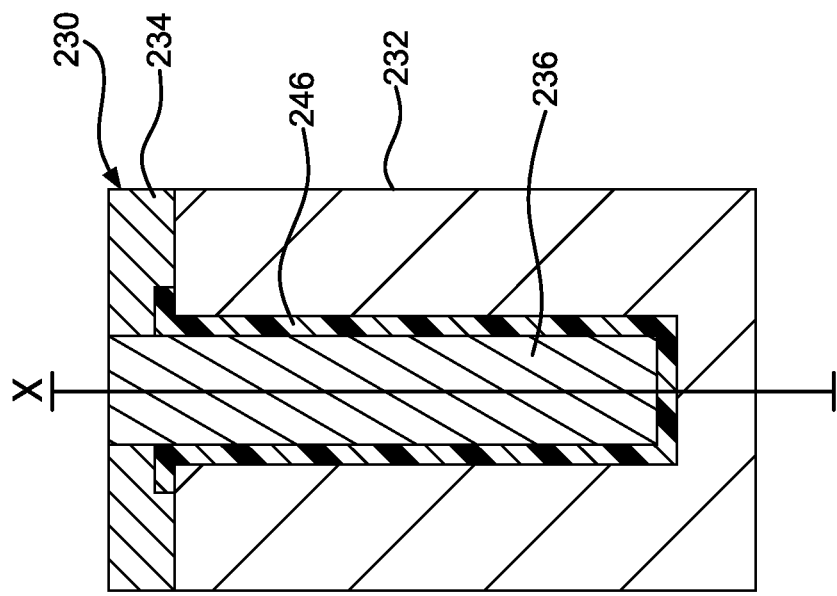
FIG. 13 is a cross sectional view showing a second stage of a molding operation of a syringe plunger in accordance with the present invention.

In FIG. 13, the molding material 246 has been introduced into the molding space 244. The molding material 246 is preferably a thermoplastic polymeric material, such as PP or COC. The molding material 246 is heated above its melting point and flows to completely fill the molding space 244. Heat may be provided by way of the heated lower plate 232 and optionally heated inner core 236 and/or upper plate 234. Optionally, additional heat sources may be used as well. In one preferred embodiment using COC or PP as the molding material 146, the lower plate 232 molding temperature is between 160 C and 210 C. The inner core 236 and/or upper plate 234 may optionally be heated to this temperature as well. Alternatively, these portions could be heated to different temperatures. In one embodiment, the molding temperature(s) that the lower plate 232 and optionally inner core 236 and/or upper plate 234 are selected to control flow of the molding material 246. In another embodiment, the lower plate 232 is heated to the minimum temperature needed to eliminate any clearances between it and the upper plate 234, so as to minimize fatigue of the material caused by repeatedly heating and cooling during molding operations.

A subsequent stage of the molding operation is shown in FIG. 14. At this stage, the lower plate 232 is cooled. This cooling causes shrinkage of the lower plate 232, giving it an inside diameter D3 greater than the outside diameter D4 of the cylindrical body 125. This, in turn, creates a clearance 250 between the lower plate 232 and the outer surface 123 of the cylindrical body 125, as shown in detail in FIG. 14A. The lower plate 232 is preferably cooled at least to a temperature so as to cause sufficient shrinkage to eliminate any potential interference between the lower plate 232 and cylindrical body 125, thus permitting extraction of the syringe plunger 124 from the molding cavity 238. In one embodiment, the lower plate 232 is cooled sufficiently to a temperature to create a clearance 250 of 10 µm. In another embodiment, the lower plate 232 is cooled sufficiently to a temperature to create a clearance 250 of 15 µm. In other embodiments the lower plate 232 could be cooled to a temperature to create a larger or smaller clearance, depending on factors such as the size of the mold 230, the type of molding material, and end product geometry. Optionally, the inner core 236 and upper plate 234 may be cooled at the same time as the lower plate 232. Also optionally, the cooling of the lower plate 232 and possibly the inner core 236 and upper plate 234 may be of a degree sufficient to cause cooling of the molding material 246 below the melting point or glass transition temperature thereof. The molding material 246 is preferably cooled below the glass transition temperature (Tg) thereof before extraction. In a preferred embodiment, entire the lower plate 232 is cooled at a uniform rate to encourage uniform setting of the molding material 246. Likewise, the inner core 236 and upper plate 234 may each be cooled at a uniform rate. In another preferred embodiment, the inner core 236, lower plate 232 and upper plate 234 are all cooled at the same uniform rate. Likewise, any combination of the inner core 234, lower plate 232 and upper plate 236, as well as any additional mold portions that may be included, can be cooled at a uniform rate. In another embodiment, the rate of cooling of any of the mold portions is utilized to control the rate at which the molding material 246 sets, in order to impart desired characteristics in the finished syringe plunger 124.

FIG. 15 shows an extraction stage of the molding operation. As shown, the molding material 246 is completely solidified to define the finished syringe plunger 124. The upper plate 234 is removed from the lower plate 232 by moving it in direction D and the plunger 124 is easily extracted from the molding cavity 238 defined in the lower plate 232 by moving it in direction D. In one embodiment, the opening 240 of the upper plate 234 is provided with draft angles to permit its removal from the collar 129 of the plunger. Alternatively, the upper plate 234 could be formed as multiple pieces, as in the embodiment of the upper plate for molding the syringe barrel 112 of FIG. 7.

Figure 16:
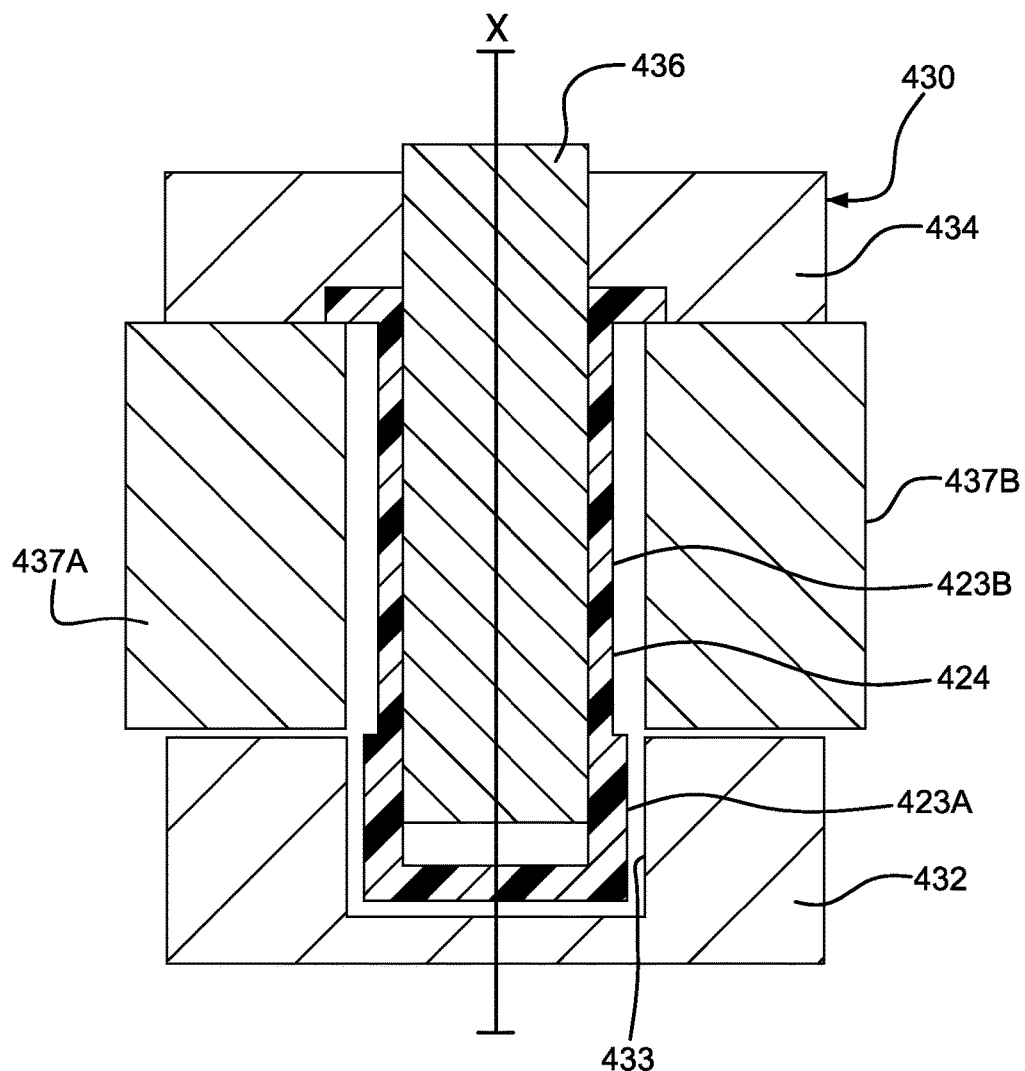
FIG. 16 is a cross sectional view showing a stage of a molding operation of another embodiment of a syringe plunger in accordance with the present invention.

Another aspect of the present invention is directed to a method of molding a product partially free of draft angles on an exterior surface thereof, such as syringe plunger 424. FIG. 16 shows an extraction stage of a molding operation of such an embodiment, analogous to the extraction stage shown in FIG. 15. As shown, a middle plate 437 is situated between lower plate 432 and upper plate 434. Lower plate 432, which forms only the lower portion of the cylindrical plunger body 425, has an inner surface 433, which is parallel to the central axis x and is formed of a material with a selected coefficient of thermal expansion to permit sufficient contraction such that the draft angle is minimized or not required in the inner surface 433 thereof in order to extract the finished plunger 424. The middle plate 437 need not be formed of a material with the selected coefficient of thermal expansion. In the embodiment shown in FIG. 16, the middle plate 437 is formed as two portions 437A, 437B to facilitate removal from the finished plunger 424. Alternatively, the middle plate 437 could include draft angles or be configured in other ways to facilitate removal. The embodiment of FIG. 16 has the advantage of minimizing the relative proportion of the molding equipment formed using the material having a selected coefficient of thermal expansion and thus reducing cost. In this respect, the size of the lower plate 432 can optionally be minimized, so as to minimize cost. In one embodiment, the lower plate 432 is configured to be a replaceable component, to be disposed of and replaced when the material has fatigued and can no longer expand and contact reliably during molding. According to this embodiment, the size of the lower plate 432 could be minimized so as to minimize costs when replacing the lower plate 432.

Figure 17:
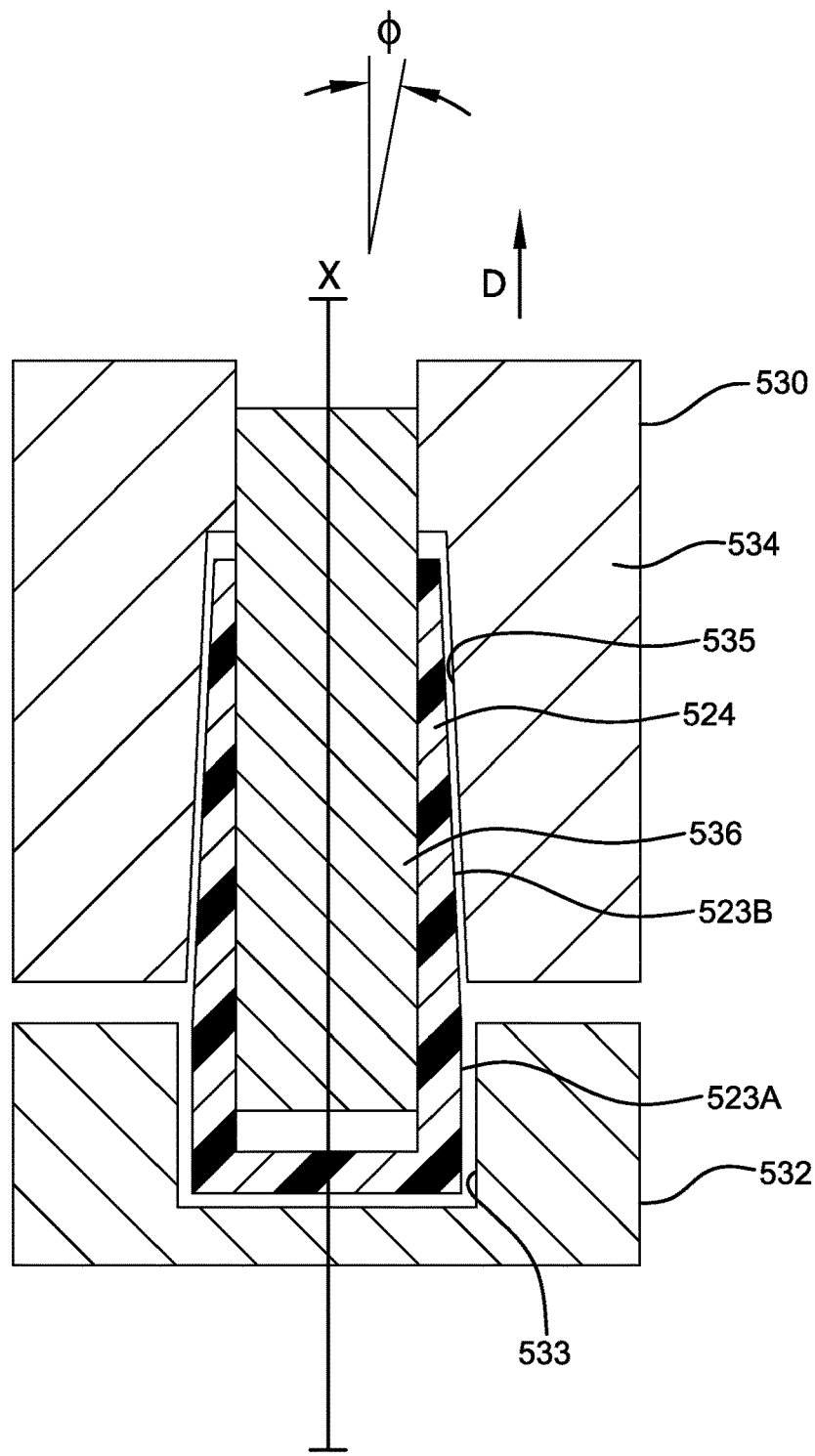
FIG. 17 is a cross sectional view showing a stage of a molding operation of another embodiment of a syringe plunger in accordance with the present invention.

FIG. 17 shows an extraction stage of another embodiment of a molding operation of a syringe plunger 524 in accordance with the present invention, analogous to the extraction stages shown in FIGS. 15 and 16. As shown, the plunger 524 of FIG. 17 differs from those described above and in that it does not include a collar. Lower plate 532 is configured similarly to the lower plate 432 of FIG. 16 and forms only the lower portion of cylindrical body 525. Inner surface 533 of lower plate 532 is parallel to central axis x and is formed of a material with a selected coefficient of thermal expansion to permit sufficient contraction such that draft angles are minimized or not required in the inner surface 533 thereof in order to extract the finished plunger 524. The molding operation of FIG. 17 differs from that of FIG. 16 in that the middle plate is omitted, and upper plate 534, which is formed as a single piece in FIG. 16, extends downward to come into contact with the top of lower plate 532, such that it takes the place of both the upper and middle plate of the embodiment of FIG. 16. The inner surface 535 of upper plate 534 is oriented at draft angle φ with respect to central axis x, such that the body 525 of plunger 524 tapers inward in an upward direction. Upper plate 534 can thus be removed from the finished plunger 524 by moving in direction D, as shown in FIG. 17. This embodiment also has the advantage of minimizing the relative proportion of the molding equipment formed of the material having the selected coefficient of thermal expansion and thus reducing cost. In this respect, the size of the lower plate 532 can optionally be minimized, so as to minimize cost. In one embodiment, the lower plate 532 is configured to be a replaceable component, to be disposed of and replaced when the material has fatigued and can no longer expand and contact reliably during molding. According to this embodiment, the size of the lower plate 532 could be minimized so as to minimize costs when replacing the lower plate 532.

The plungers 424, 524 of FIGS. 16 and 17 could be configured and produced, in all other respects, the same as that of FIGS. 12-15.

Another aspect of the present invention is directed to a method of producing a syringe 110 using one or more of the methods for molding a barrel 112 and/or plunger 124, 424, 524 described above. In one embodiment, the barrel 112 and plunger 124, 424, 524 are each molded in accordance with one of the methods described above, and assembled to produce a syringe 110, such as that shown in FIG. 2.

According to one embodiment, the barrel 112 of FIGS. 3-7 is assembled with the plunger 124 of FIGS. 12-15 to produce a syringe. According to such an embodiment, the inner diameter of cylindrical barrel body 114 and outer diameter of plunger cylindrical body 125 may be substantially equal. The inner surface 115 of the cylindrical barrel body 114 and the outer surface 123 of the plunger cylindrical body 125 are each substantially free of draft angles, so that the plunger 124 can easily slide within the barrel 112.

According to another embodiment, the barrel 112 of FIGS. 3-7 is assembled with the plunger 424 of FIG. 16 or the plunger 524 of FIG. 17 to produce a syringe. According to such an embodiment, a first portion 423A, 523A of the outer surface 423, 523 of the plunger cylindrical body 425, 525, which is formed by the lower plate 432, 523 is substantially free of draft angles and seams, contacts the inner surface 115 of barrel cylindrical body 114. The inner diameter of the first portion 423A, 523A of outer surface of cylindrical barrel body 414 and outer diameter of plunger cylindrical plunger body 125 are substantially equal. The plunger 424, 524 can easily slide within the barrel 112. The second portion 423B, 523B of the outer surface 423, 523 of plunger cylindrical body 425, 525, which is formed by middle plate 437 in the embodiment of FIG. 16 or upper plate 534 in the embodiment of FIG. 17, is has a smaller diameter than first portion 423A, 523A so that it does not contact the inner surface 115 of barrel cylindrical body 414 and does not interfere with sliding of the plunger 424 within the barrel 112.

According to one embodiment, a syringe 110 is assembled as described in any of the embodiments described above, without the provision of a lubricity coating. The matching diameters of the barrel cylindrical body 114 and plunger cylindrical body 125, 425, 525 and the lack of draft angles therein facilitates sliding of the plunger 124, 424, 524 within the barrel 112, such that a lubricity coating is not needed. In another embodiment of the invention, a lubricity coating could be provided to further facilitate sliding.

According to another embodiment of the invention, a plurality of syringes are produced by assembling a plurality of barrels 112 and a plurality of plungers 124, 424, 524. The inner diameter of each barrel cylindrical body 114 and the outer diameter of each plunger cylindrical body 125, 425, 525 or just the first portion 423A, 523A of the outer surface 423, 523 of the plunger cylindrical body 425, 525 are measured after molding, and each barrel 112 is matched with a plunger 124, 424, 524 having a cylindrical body 125, 425, 525 with an outer diameter substantially closest to the inner diameter of the barrel cylindrical body 125, 425, 525. This optimizes the sliding capabilities of the plunger 124, 424, 524 within the barrel 112.

In one embodiment, the barrel 112 and plunger 124, 424, 524 are robotically removed from the molds 130, 430, 530. This eliminates any scratches or other defects that could be caused by manual removal, to further optimize the sliding capabilities of the plunger 124, 424, 524 within the barrel 112.

Another aspect of the present invention relates to a syringe, which may be a prefilled syringe produced in accordance with one or more of the methods described above. The syringe can take on various configurations. In one embodiment, the syringe is configured and/or produced as disclosed in U.S. Ser. No. 61/359,434. Syringes in accordance with the present invention are particularly advantageous for use as prefilled syringes, because as described in detail above, the outer diameter of the plunger 124, 424, 524 and inner diameter of the barrel 112 can be substantially equal, eliminating any clearances therebetween that could result in leakage.

Figure 19:
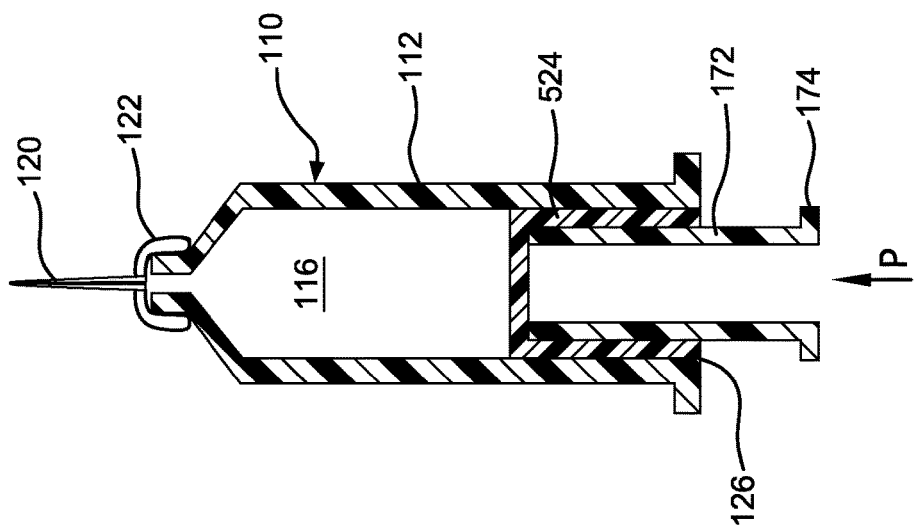
FIG. 19 is a cross sectional view of the syringe of FIG. 18 as prepared for administration of a dosage.
Figure 18:
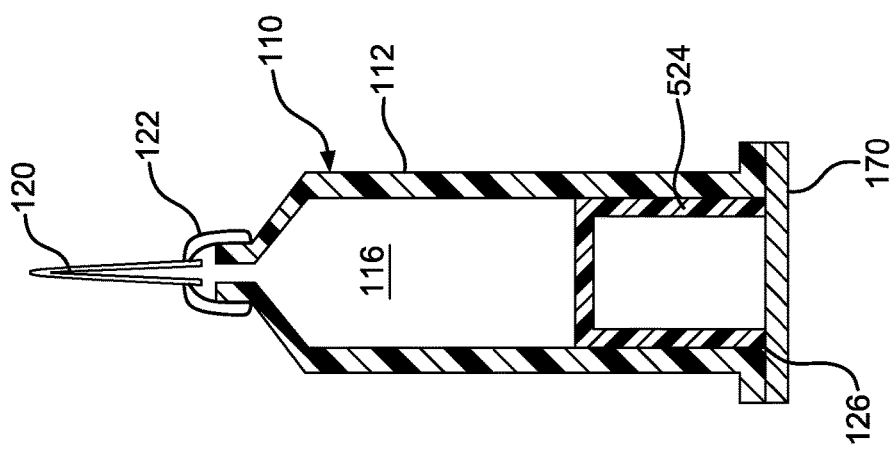
FIG. 18 is a cross sectional view of a syringe produced in accordance with the present invention in a storage configuration.
Figure 20:
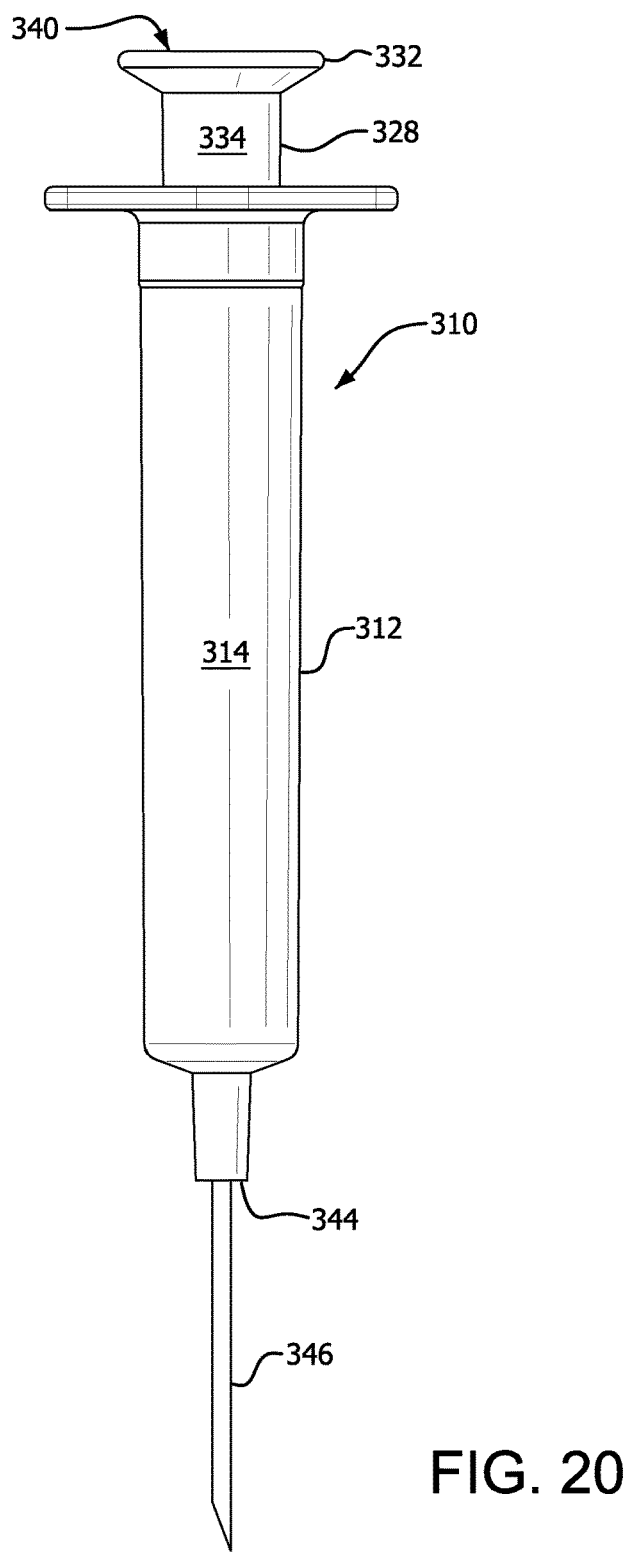
FIG. 20 is a side elevation of a syringe according to an embodiment of the invention.

One embodiment of a prefilled syringe in accordance with the present invention is shown in FIGS. 18 and 19. The illustrated syringe 110 includes a barrel 112 produced in accordance with FIGS. 3-7 and a plunger 524 produced in accordance with FIG. 17. FIG. 18 shows the assembled prefilled syringe 110 with the plunger 524 housed within the barrel 112. A seal 170, which can be formed as a foil or a thin plastic layer, is affixed over the open end 126 of the barrel 112 to maintain sterility of the product contained within the prefilled syringe 110. Prior to administering the product contained within the syringe 110, the seal 170 is removed, as shown in FIG. 19. Because the plunger 524 of the syringe 110 shown in FIGS. 18 and 19 does not include a collar to assist depressing the plunger 524, a depressor 172 can be provided as separate element. After the seal 170 is removed, the depressor 172 is inserted into the plunger 524, as shown in FIG. 19. The depressor 172 includes a collar 174 that protrudes from the end of the syringe when assembled in the configuration of FIG. 19, and enables a user of the syringe 110 to push the plunger 524 in direction P by pressing thereon to administer the product contained within the syringe 110.

In another embodiment, the syringe 110 could be provided as a prefilled, sealed device, similarly to that of FIGS. 18 and 19, but the depressor 172 could be omitted. Other embodiments of plungers in accordance with the invention, such as those of FIGS. 12-16, could be used in place of the plunger shown in FIGS. 18 and 19.

Figure 9:
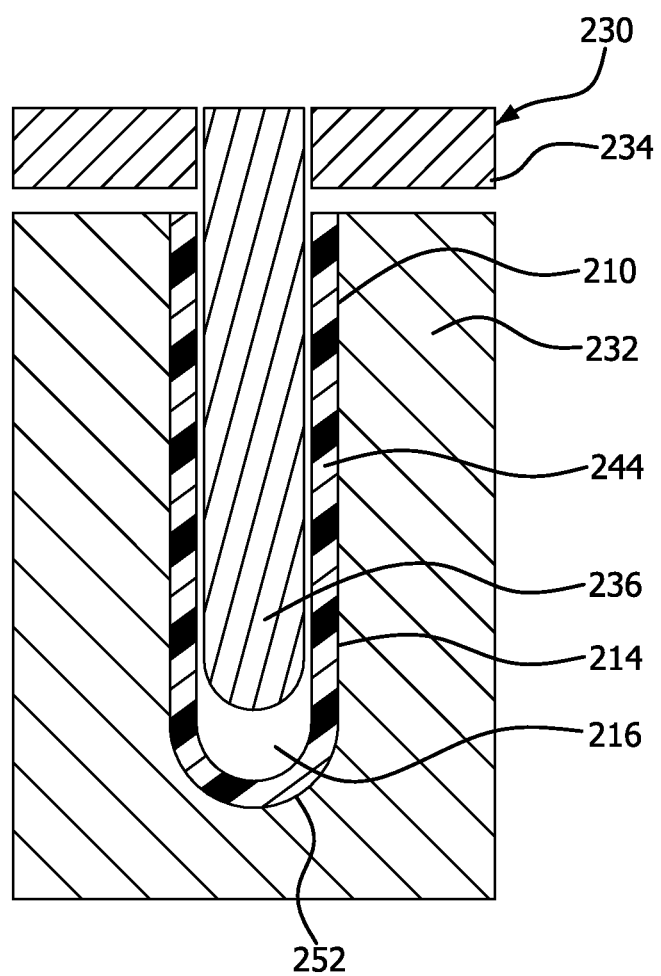
FIG. 9 is a cross sectional view showing a stage of a molding operation of a test tube in accordance with the present invention.

While the method of the invention is described above with respect to a syringe barrel and plunger, it can also be employed for various other products formed using a mold having an inner core portion. For example, other products having tubular shapes or hollow interiors can be formed by an analogous method to that described above. Modifications to the configuration of the molding equipment would be within the purview of one of ordinary skill in the art based on the above description. FIG. 2 shows a test tube 610 formed using a process analogous to that described above. As shown, the test tube 610 has a cylindrical body 614 defining an interior 616. FIG. 9 shows a stage of a molding operation of such a test tube 610 in accordance with the present invention, during which the finished test tube 610 is removed from the molding equipment 630. As shown, the mold 630 is similar to that described above with respect to FIGS. 3-6, with the exception of the fact that the shape of the molding space 644 corresponds to that of test tube 610 and includes a rounded, closed off bottom portion 652, whereas the bottom portion 652 of the molding space of FIGS. 3-6 defines an opening for passage of a dosage administered using the syringe 10. In another embodiment, the lower plate 632 and/or upper place 634 could be provided as two or more pieces, in an analogous manner to that of the embodiment of FIG. 7.

Other aspects of the invention are directed to a syringe 110 (FIGS. 1-9 and 18-19), 310 (FIG. 20-25), or 1282 (FIG. 35), each optionally molded in accordance with the above. The inventors expressly contemplate that the molding method described above is useful for making any type of syringe.

Referring to FIGS. 20-25, the syringe assembly 310 includes a barrel 312 including a generally cylindrical side wall 314. The side wall 314 is made of substantially rigid thermoplastic material in this embodiment, though the side wall 314 alternatively can be made of thermosetting material, glass, metal, other materials, or any combination of materials, without limitation. The side wall 314 defines a bore 316 for containing a liquid.

The syringe assembly 310 includes a piston 318 (seen in FIGS. 21-23) having a leading face 320, a trailing face 322, and a side edge 324 configured to movably seat in the bore 316. In the illustrated embodiment, the piston 318, including its side edge 324, is made of substantially rigid thermoplastic material, though the piston 318 alternatively can be made of thermosetting material, glass, metal, other materials, or any combination of materials, without limitation. In particular, instead of being made of substantially rigid material, at least the side edge 324 can be made of elastomeric material, either co-molded with the material of the remainder of the piston 318 or provided as a separate part and assembled. The provision of a separate, elastomeric piston surface or plunger tip 324 assembled with a more rigid core or plunger body is known in the art.

Preferably, a lubricant 326 is deposited on the side edge 324 of the piston 318, the bore 314, or both. In a particularly preferred embodiment, the lubricant 326 is deposited by PECVD, for example as explained herein.

In the illustrated embodiment, the piston leading face 320 is convex. A convex leading face 320 having a shape complementary to the shape of the portion of the barrel 312 adjacent to the dispensing opening 344 is particularly contemplated, so when the piston leading face 320 is fully advanced toward the dispensing opening 344 the volume enclosed between these parts is small, to limit the amount of dispensed material remaining in the syringe 310 after dispensing is complete.

In the illustrated embodiment, the piston trailing face 322 is concave. The trailing face 322 alternatively could be any shape, although it may be advantageous to provide a concave piston trailing face in combination with a convex leading face 320 and a relatively thin piston 318 to reduce the amount of material used to make the piston 318. It is further contemplated that a relatively thin, curved piston 318 will be more flexible than a thicker, cylindrical piston, allowing it to move more easily in the barrel 312 and to conform to minor irregularities in roundness of the barrel 312 or the piston 318 as it is advanced in the barrel.

In the illustrated embodiment, the piston side edge 324 has a clearance from the bore 316. The clearance should be small enough to prevent leakage of the contents of the syringe assembly 310 past the side edge 324, but large enough so the piston 318 can slide smoothly through the syringe barrel. The radial clearance is preferably greater for a relatively rigid side edge 324 than is common for elastomeric plunger tips, which commonly have an interference fit (providing near-zero clearance when the parts are assembled). Elastomeric plunger tips must flex to allow the plunger tip to be advanced in the barrel, and this flexing increases the friction between the piston 318 and the barrel 312. In the present embodiment, the clearance between the plunger and the syringe barrel is preferably from about 10 to about 15 µm (micrometers).

The bore 316 of the barrel 312 preferably has an axial draft angle θ (theta) as shown in FIG. 1A of from 0° to 0.5° (i.e. zero to 30 minutes of arc), optionally from 0° to 0.25°, optionally from 0° to 0.16°, optionally from 0° to 0.06°, optionally from 0° to 0.03°, optionally from 0° to 0.014°, optionally from 0° to 0.01° optionally either substantially or exactly zero degrees. The acceptable draft angle is in part a function of the draw length—the length of travel of the piston 318 along the syringe barrel when fully dispensing the contents to the extent allowed by the geometry of the syringe.

The nominal draft angle (θ) and its tolerance can be such that the clearance between the piston 318 and the syringe barrel is between 10 µm and 15 µm over the draw length—the length of travel of the piston 318 along the syringe barrel 312. Thus, the change in clearance can be 5 µm over the draw length. For example, the above draft angles provide the changes in clearance between the piston 318 and the barrel 318 (on each side) shown in the Draw Length table.

| Draft angle | | Draw Length (mm) | | | |
| --- | --- | --- | --- | --- | --- |
| | | 5 | 10 | 20 | 30 |
| θ, deg. | tan (θ) | Change of Clearance (µm) | | | |
| 0 | 0 | 0 | 0 | 0 | 0 |
| 0.01 | 0.00017 | 0.8 | 1.7 | 3.3 | 5 |
| 0.014 | 0.00025 | 1.3 | 2.5 | 5 | 7.5 |
| 0.03 | 0.0005 | 2.5 | 5 | 10 | 15 |
| 0.06 | 0.001 | 5 | 10 | 20 | 30 |
| 0.16 | 0.0028 | 14 | 28 | 56 | 84 |
| 0.25 | 0.00436 | 22 | 44 | 88 | 132 |
| 0.5 | 0.00873 | 44 | 88 | 176 | 264 |

Thus, for example, if the draft angle θ is uniformly 0.16°, the change of clearance between the piston 318 and the barrel 312 over the draw length is 14 µm. The tangent of the draft angle (θ) is equal to the change in clearance divided by the draw length. A large draft angle over a long draw length increases the minimum clearance by a relatively large amount at the beginning of piston travel (assuming a positive draft angle and dispensing out of the syringe, as opposed to drawing fluid in). Thus, for longer draw lengths, smaller draft angles are desirable. Also, a zero draft angle is suitable for any draw length, and will provide a uniform clearance between the piston 318 and barrel 312.

Although positive or zero draft angles are preferred for the interior of a syringe barrel, negative draft angles of the same values and ranges will provide the same change of clearance during dispensing, except that the draft angle will be smallest at the beginning of dispensing.

The portion of the barrel 312 traversed by the piston 318 will depend on the volume of contents to be delivered by the syringe 310. Commonly, the portion of the barrel 312 traversed by the piston 318 will be substantially less than the full length of the barrel 312. For a single-use prefilled syringe, the manufacturer will effectively determine the portion of the barrel 312 traversed by the piston 318 according to how much of the barrel 312 is filled by the contents to be delivered. Behind the fully drawn piston 318 of the filled syringe, the clearance can be greater than indicated above. In fact, a greater clearance behind the fully drawn piston is desirable to facilitate insertion of the piston 318 into the barrel 312 during assembly by opening up the back of the barrel 312. Consequently, the draft angle can be larger behind the fully drawn piston 318 than beside or in front of it.

Figure 21:
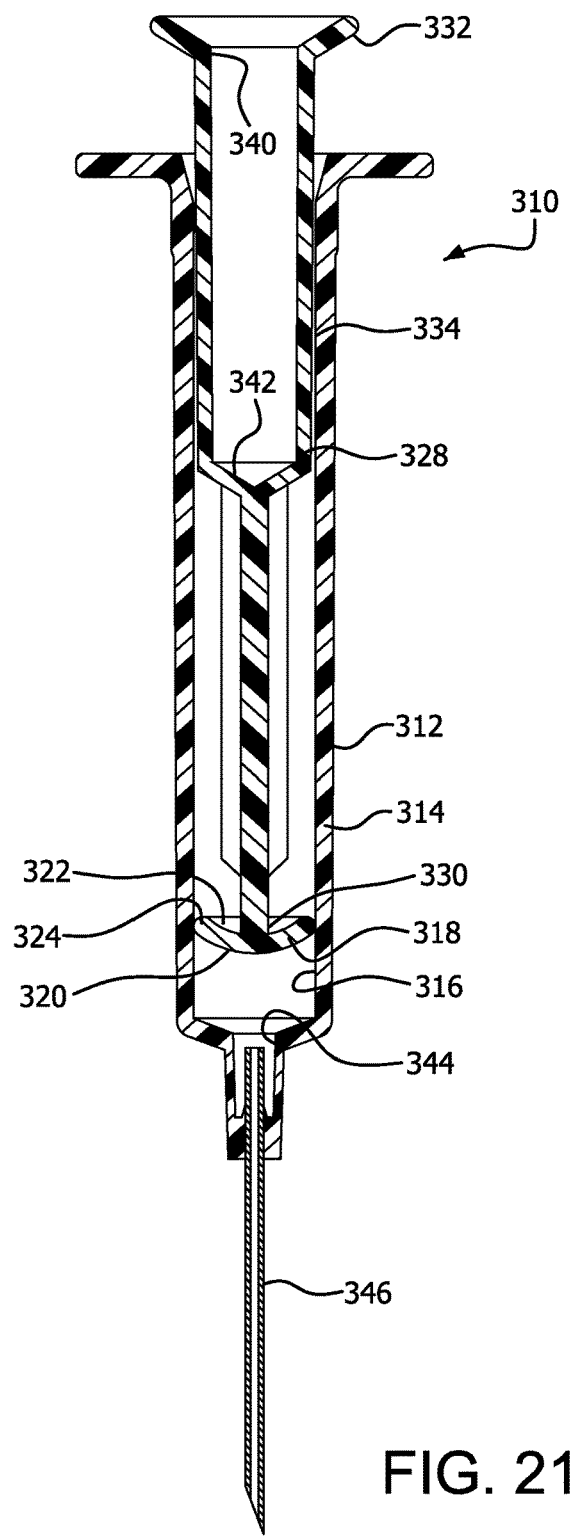
FIG. 21 is a longitudinal section of the embodiment of FIG. 20.

Optionally, the piston side edge 324 is convex in an axial plane, as illustrated in the present figures, particularly FIG. 21. This curvature of the side edge 324 reduces the contact area between the side edge 324 and the barrel 312, thus reducing sliding friction or opportunities for the side edge 324 and a portion of the barrel 312 to catch due to surface irregularities in either or both of them.

In the illustrated embodiment, the barrel 312 is a single injection molded thermoplastic part (apart from any lubrication or other layers). This is advantageous from the point of view of easy manufacture, though it is not essential, and a two-part or multi-part barrel is also contemplated alternatively. For example, a hub for attaching the hypodermic needle 346 could be provided as a separate part, or a Luer, Luer lock, or other type of coupling could be provided between the hypodermic needle 346 and the barrel 312. Optionally, each single molded thermoplastic part is made of a single, uniform material. Again, however, alternative embodiments are contemplated in which one or more of the parts are made from a composite, heterogeneous, or layered material.

Figure 22:
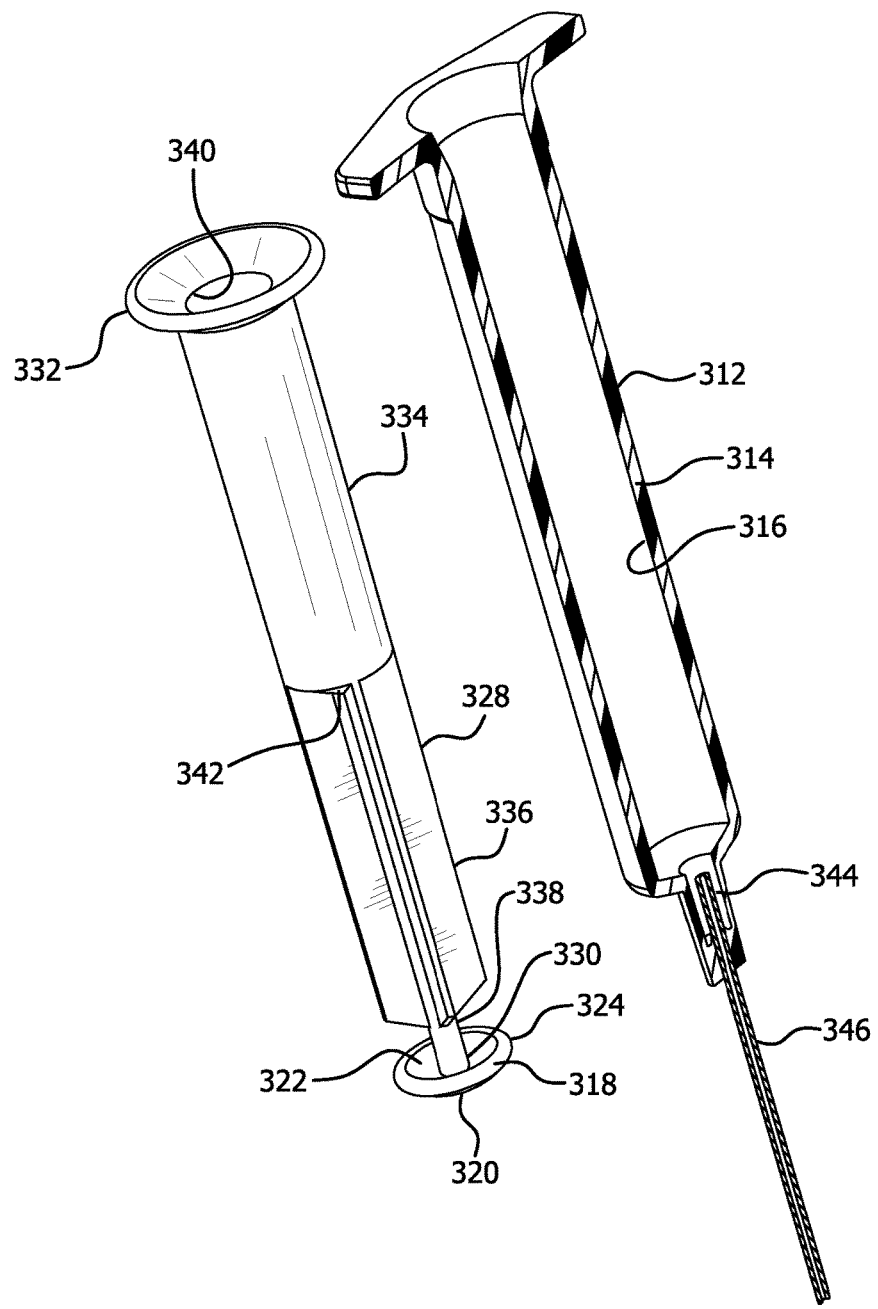
FIG. 22 is an exploded perspective view, partly in section, of the embodiment of FIG. 20.
Figure 23:
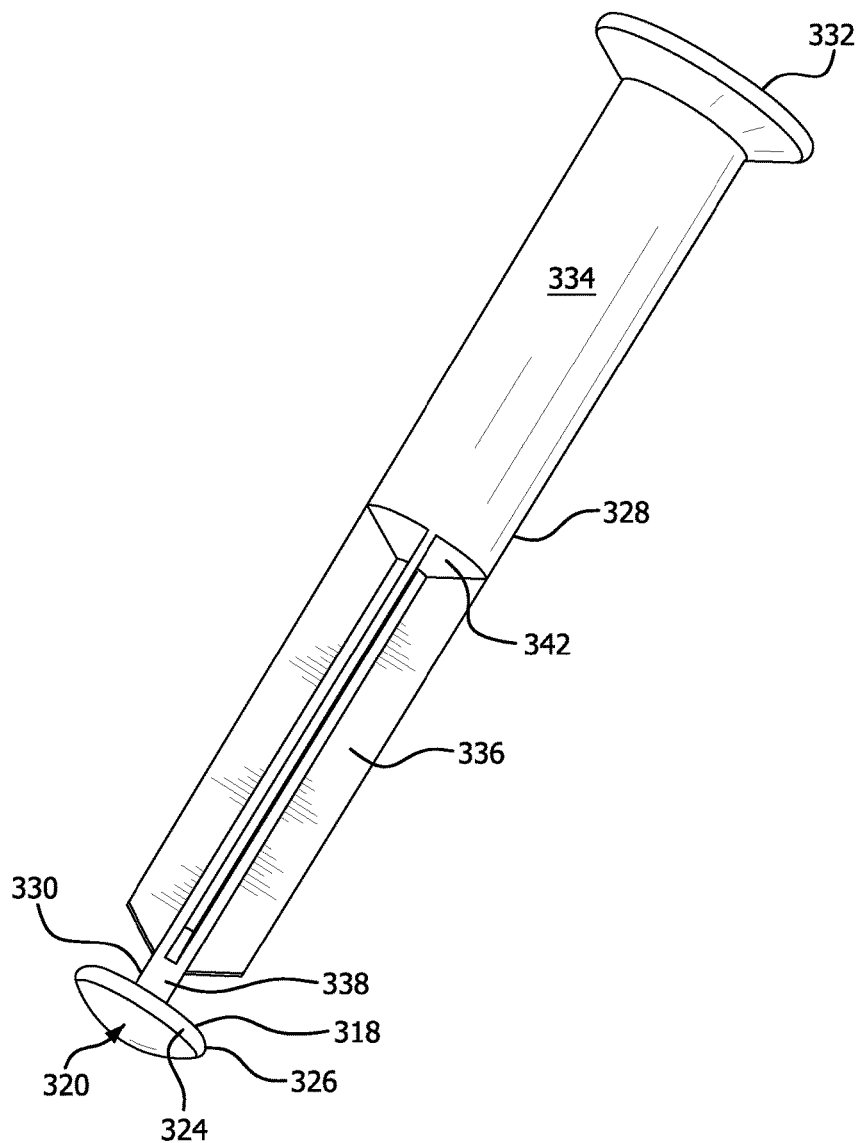
FIG. 23 is a perspective view of the plunger of the embodiment of FIG. 20.
Figure 25:
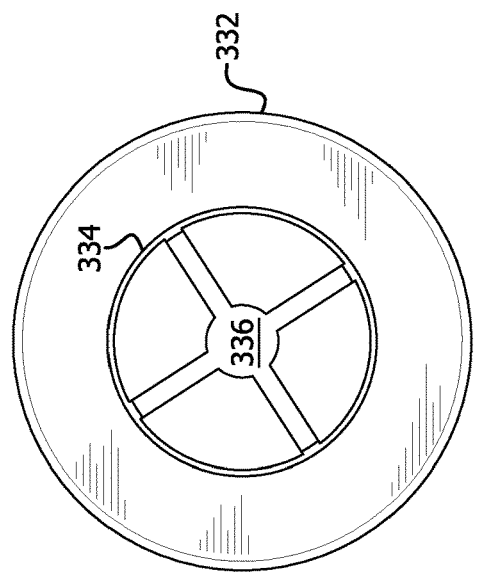
FIG. 25 is a view similar to FIG. 24 of the plunger of the embodiment of FIG. 20.
Figure 24:
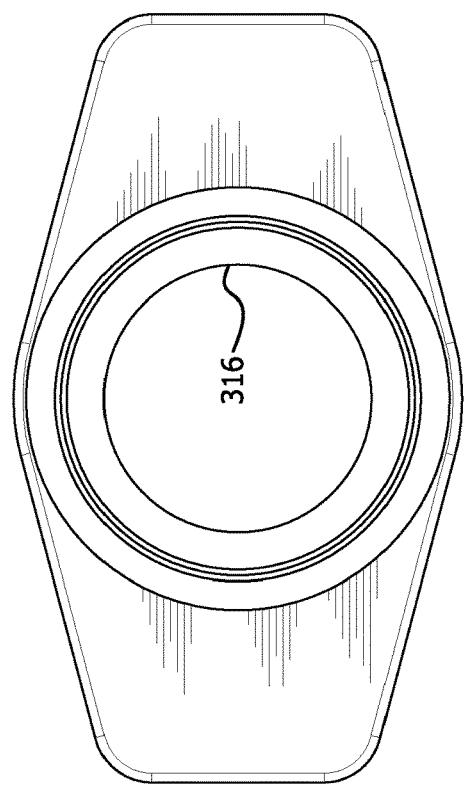
FIG. 24 is an isolated back-end elevational view of the syringe barrel of the embodiment of FIG. 20.

Referring particularly to FIGS. 21-23, optionally, the piston 318 is associated with a stem or pushrod 328 for advancing the piston 318 in the bore 316. Optionally, the piston 318 and stem 328 are a single injection molded thermoplastic part, although they can optionally be provided as two or more parts. Optionally, each single molded thermoplastic part is made of a single, uniform material. Again, however, alternative embodiments are contemplated in which one or more of the parts are made from a composite, heterogeneous, or layered material. For example, the thermoplastic molding defining the piston 318 and stem 328 can include a first shot of more slippery material to ease advance of the piston 318 in the barrel 312

In the illustrated embodiment, the stem 328 has a first end portion 330 connected to the piston 318 and an opposed second end portion 332 projecting from the barrel 312. A portion of the stem 328 between its first and second ends has a tubular section 334 with a maximum radial clearance from the bore 316 of less than 1 mm. In the illustrated embodiment, the tubular section 334 of the stem 328 is adjacent to its second end portion 332. The tubular section 334 can be sized and positioned on the part to prevent the stem 328 and piston 318 from skewing as the piston 318 is advanced in the barrel 312.

Additionally, in the illustrated embodiment a portion of the stem 328 between its first and second end portions 330, 332 has a generally cross-shaped section 336. In this embodiment the cross-shaped section 336 of the stem 328 is adjacent to its first end portion 330. In the illustrated embodiment, the closed end 342 of the tubular section 334 merges into the generally cross-shaped section 336 of the stem 328.

A portion of the stem 328 between its first end portion 330 and its generally cross-shaped section 336 has a rod section 338 having a diameter less than half of the diameter of the bore 316. This diameter limitation is not critical, however, and a larger or smaller diameter can be provided. The tubular section 334 has an open end 340 and a closed end 342 disposed within the syringe barrel.

In the illustrated embodiment, the barrel 312 has a dispensing opening 344 and the syringe assembly further comprises a hypodermic needle 346 operatively connected to the dispensing opening 344.

Syringe barrels and pistons can be treated by PECVD (plasma enhanced chemical vapor deposition) to provide (1) barrier coating of the barrel and/or plunger, (2) lubricity coating of the barrel and/or plunger, or (3) surface modification of the barrel or plunger to minimize protein adsorption. The PECVD treatment of syringe barrels is described in U.S. Publ. Appl. No. 2010/0298738 A1, published Nov. 25, 2010, issued as U.S. Pat. No. 7,985,188 on Jul. 26, 2011, incorporated by reference herein. The PECVD treatment of syringe plungers is described below.

Referring now to FIGS. 26-35, embodiments will be described for providing PECVD layers on a syringe piston or other structure partially or entirely slidable within a tube in sealing relation. These embodiments are suitable providing layers on any of the pistons or plungers such as 124 of FIG. 2, the plungers of FIGS. 10A through 10G, the plungers 524 of FIGS. 18-19, the piston 318 of FIGS. 20-25, the plunger or generally cylindrical article 1258 of FIGS. 26-30, the stopper 1282 of FIGS. 31, 32, 34, and 35, or the septum 1310 of FIG. 33.

Figure 26:
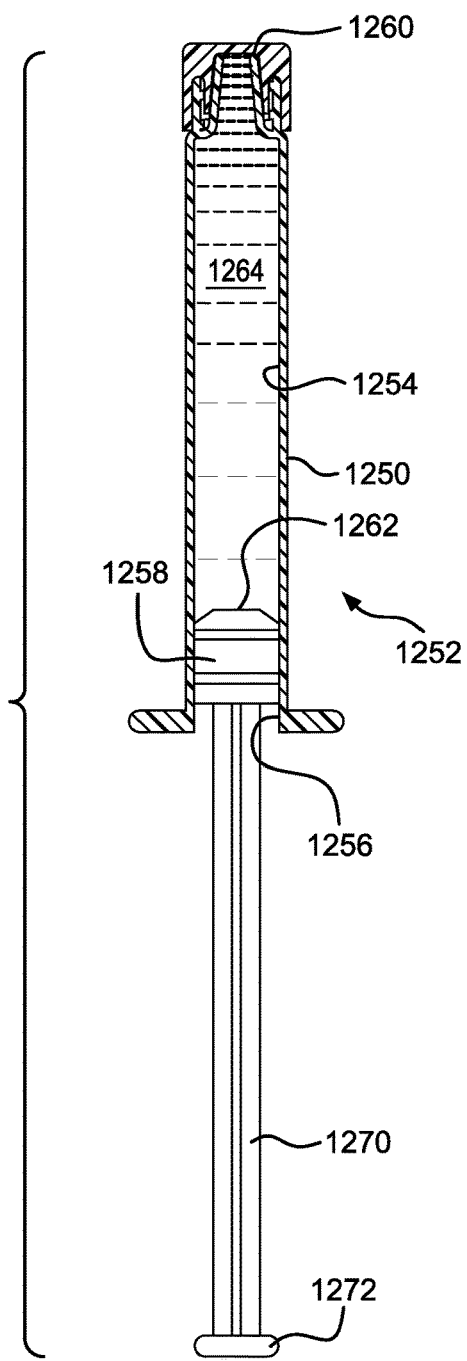
FIG. 26 is a longitudinal section of a syringe according to the prior art.
Figures 27, 28:
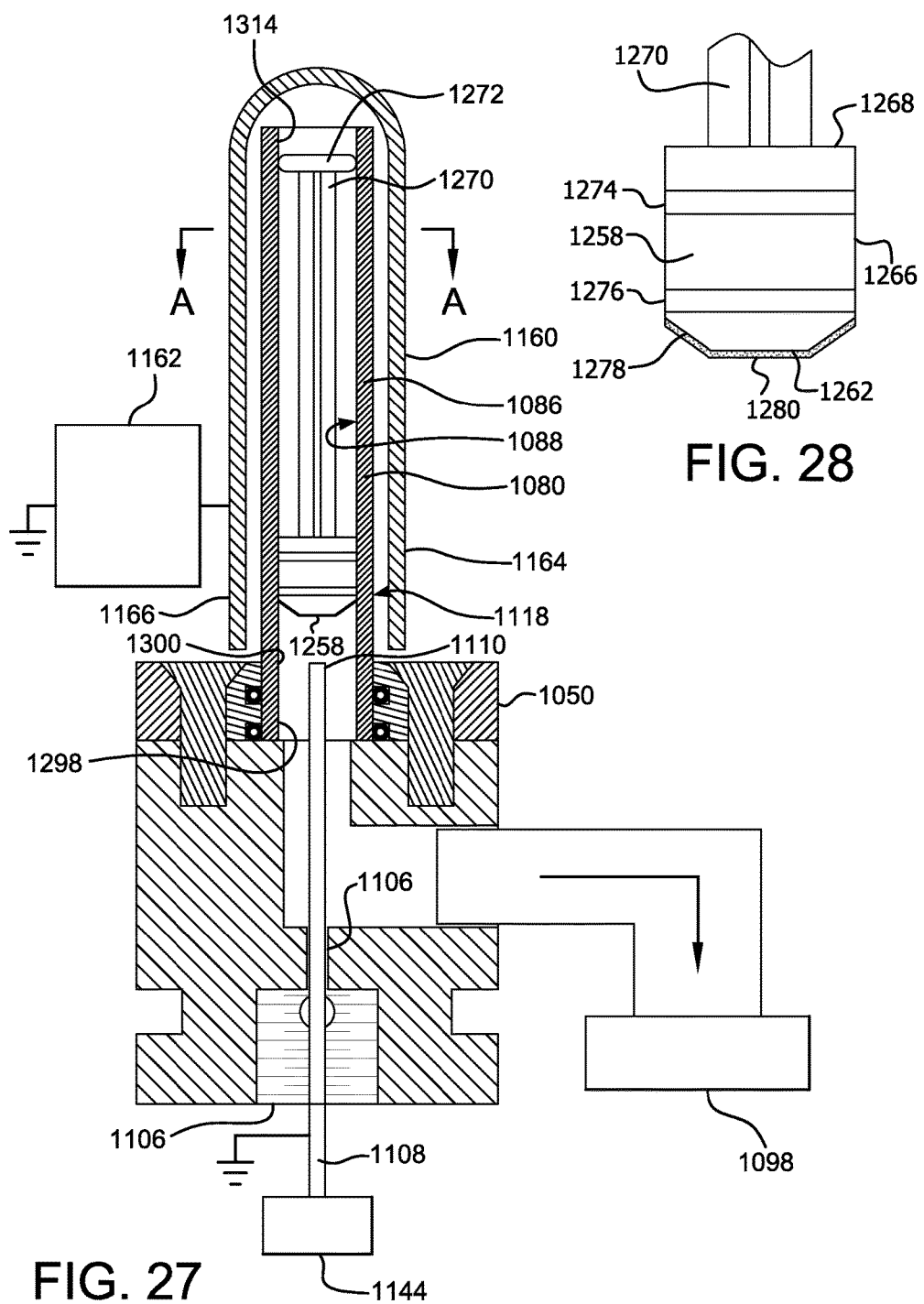
FIG. 27 is a longitudinal section of apparatus for forming a layer on a syringe plunger.
FIG. 28 is an enlarged detail view of the syringe plunger shown in FIG. 2, illustrating its parts.

Referring to FIGS. 26 and 28, a typical syringe 1252 on which the present invention can be practiced includes a syringe barrel 1250 having an interior surface 1254, a open end 1256, a plunger 1258, and a front end 1260. The syringe barrel 1250 can optionally be filled with contents 1264. The syringe plunger or plunger 1258 has a generally circular front portion 1262, a generally cylindrical side portion 1266, a generally circular back portion 1268, and a plunger rod. The illustrated embodiment has optionally raised, optionally integral piston rings 1274 and 1276, which in this embodiment are part of the side portion 1266, and a chamfer 1278, which in this embodiment is a peripheral front portion 1262. The front portion 1262 is defined as the portion of the plunger 1258 which is normally in contact with the contents 1264 of the syringe, when present.

It is desirable that the front portion 1262 of the plunger be provided with a barrier layer 1280 to prevent constituents of the plunger 1258 from leaching into the contents 1264 of the syringe or vice versa, particularly in the case of a prefilled syringe 1252. A typical SiOx barrier layer 1280 and how to apply it are extensively explained, for example, in U.S. Publ. Appl. No. 2010/0298738 A1, published Nov. 25, 2010, issued as U.S. Pat. No. 7,985,188 on Jul. 26, 2011. The latter publication and patent are incorporated here by reference to show suitable barrier and lubricity layers and how they can be applied. But it may be desirable in certain cases that the side portion 1266 be free of the SiOx layer.

Similarly, it is desirable that the side portion 1266 be provided with a lubricious or lubricity layer to reduce the breakout and sliding forces needed to advance the plunger 1258 in the barrel 1250, as when dispensing the contents of the syringe 1252. But it may in some instances be desirable to keep the front portion 1262 of the plunger 1258 free of the lubricious layer, to prevent constituents of the layer from escaping into the contents of the syringe 1252.

Therefore, the present methods of all embodiments allow customization of layers applied to a workpiece, such as the plunger 1258, to coat portions desired to be coated and avoid layer portions not to be coated.

A method according to an embodiment of the invention for selectively layer a syringe plunger 1258 using plasma enhanced chemical vapor deposition is illustrated in FIGS. 27 and 28. A syringe plunger 1258 is provided having a generally circular front portion 1262 positioned for contacting contents 1264 of a syringe barrel 1250 and a generally cylindrical side portion 1266 adapted for slidably contacting a syringe barrel 1250. A generally tubular plunger holder 1080 is provided having a front opening 1082 and an inner sidewall 1088 extending from the front opening 1082.

The syringe plunger 1258 is placed in the plunger holder 1080, oriented with the front portion of the syringe plunger 1258 facing the front opening 1082 of the plunger holder 1080 and the side portion 1266 of the syringe plunger 1258 contacting the inner sidewall 1088 of the plunger holder 1080.

The front portion of the syringe plunger 1258 is contacted with a layer forming reactive gas. Plasma is formed in the plunger holder 1080 adjacent to the front portion 1262 of the syringe plunger 1258. The conditions are such as to deposit a barrier layer 1280 selectively on the front portion 1262 of the syringe plunger 1258, using plasma enhanced chemical vapor deposition.

The resulting coated articles can be assembled with other components, for example an assembly of the generally cylindrical article 1258 according to any embodiment with a push rod 1270. In one alternative, the plunger 1258 can be secured to a push rod 1270 while depositing the at least one layer 1280.

An assembly of the generally cylindrical article 1258 with a syringe barrel 1250 and push rod 1270 is contemplated.

An assembly of the generally cylindrical article 1258 with a syringe barrel 1250, push rod 1270, and end cap 1260 is contemplated.

An assembly of the generally cylindrical article 1258 with a syringe barrel 1250, push rod 1270, and hypodermic needle is contemplated.

An assembly of the generally cylindrical article 1258 with a syringe barrel 1250, push rod 1270, hypodermic needle, and needle shield is contemplated. In any of the above assemblies, the generally cylindrical article 1258 can be configured to function as a plunger slidable within the barrel 1250. The syringe barrel 1250 optionally also has a PECVD treated interior portion.

Representative apparatus for carrying out this method is shown in FIG. 27, which provides a PECVD apparatus including a vessel holder 1050, an counter electrode 1108, an outer electrode 1160, and a power supply 1162. A plunger holder 1080 seated on the vessel holder 1050 with a plunger 1258 in place defines a plasma reaction chamber, which optionally can be a vacuum chamber. To prevent the plunger 1258 from being drawn downward, its thumb pad 1272 optionally can engage the open end (126) of the plunger holder 180, an internal step or a projection of the plunger holder 1080 or otherwise be restrained with respect to the holder. A source of vacuum 1098 and a reactant gas source 1144 can be supplied to facilitate PECVD.

The PECVD apparatus of any embodiment can be used instead for atmospheric-pressure PECVD, in which case the plasma reaction chamber does not need to function as a vacuum chamber.

In the embodiment illustrated in FIG. 27, the vessel holder 1050 comprises a gas inlet port 1104 for conveying a gas into a vessel seated on the vessel port. The gas inlet port 1104 has a sliding seal 1106, which can seat against a cylindrical probe 1108 when the probe 1108 is inserted through the gas inlet port 1104. The probe 1108 can be a gas inlet conduit that extends to a gas delivery port at its distal end 1110. The distal end 1110 of the illustrated embodiment can be inserted into the plunger holder 1080 for providing one or more PECVD reactants and other process gases.

FIGS. 18 and 19 thus show apparatus for carrying out a method for selectively layer an end portion 1262 of a generally cylindrical article 1258 using plasma enhanced chemical vapor deposition. The method can include several steps. A generally cylindrical article 1258 is provided having an end portion 1262 and a generally cylindrical side portion 1266. A holder 1080 is provided having a first opening 1298 and defining a bore 1300 extending from the first opening 1298. The article 1258 is placed at least partially in the bore 1300, oriented with its end portion 1262 facing the first opening 1298 of the holder 1080 and its side portion 1266 contacting the bore. At least one layer such as 1280 is applied selectively on the end portion 1262 of the article 1258 by plasma enhanced chemical vapor deposition of at least one layer forming precursor, supplied by the source 1144.

Optionally, the push rod 1270 further comprises a thumb pad 1272. The thumb pad 1272 can be sized to fit at least partially within the bore 1300, for example with low clearance within the bore 1300.

Plasma enhanced chemical vapor deposition can be carried out, for example, with reference in particular to FIG. 27, as well as analogous FIGS. 31 and 35, by seating the first opening 1298 of the holder 1080 in operative relation on a PECVD apparatus comprising a vacuum source 1098 and a source 1144 of precursor gas before depositing the at least one layer 1280.

Optionally, the article 1258 is placed at least partially in the bore 1300, forming an article-bore assembly, before the first opening 1298 of the holder 1080 is seated on the PECVD apparatus. The article-bore assembly protects the article 1258 lodged within the bore, preventing any contamination of the surface to be coated before layer, and preventing the layer 1280 from being disturbed when the part is handled after layer. After forming the article-bore assembly, and before seating the article-bore assembly on the PECVD apparatus, the article-bore assembly can be transported to the PECVD apparatus, and the article can be protected during such transporting.

After the at least one layer is deposited, the article-bore assembly can be unseated, optionally while remaining assembled, and transported away from the PECVD apparatus.

Optionally, the generally cylindrical article 1258 can be removed from the article-bore assembly after the article-bore assembly is transported away from the PECVD apparatus. If the bore is open at the first opening 1298 on one end and a second opening 1314 on the other end, the generally cylindrical article 1302 can be removed from the article-bore assembly by pushing it through the first opening 1298. This can be done, for example, with an object inserted into the bore 1300 through the second opening.

Figure 30:
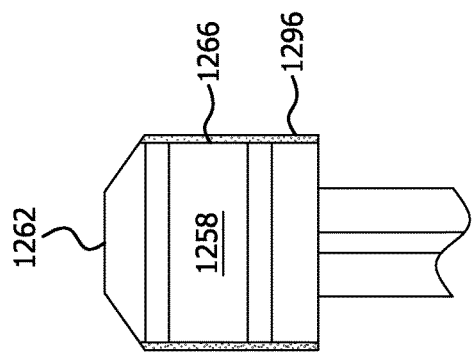
FIG. 30 is an enlarged detail view of the syringe plunger shown in FIG. 4, illustrating its parts.
Figure 29:
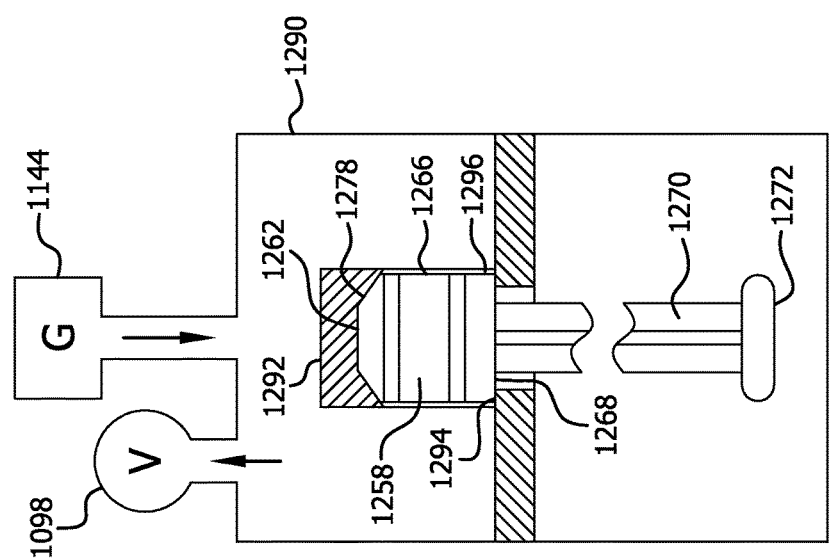
FIG. 29 is a schematic sectional view of alternative apparatus for forming a layer on the side of a syringe plunger.

Another aspect of the invention, illustrated in FIGS. 29-30, is a method for selectively layer the side portion of a syringe plunger 1258. A syringe plunger 1258 is provided having a generally circular front portion 1262 adapted in an assembled syringe 1252 for contacting contents of a syringe barrel 1250. The plunger 1258 has a generally cylindrical side portion 1266, adapted for slidably contacting a syringe barrel 1250 (FIG. 26), and a generally circular back portion 1268. FIG. 29 also shows that the generally cylindrical article 1258 optionally is secured to a push rod 1270 and supported on a holder 1294 during the layer step, and optionally can be removed from the holder 1294 by handling the push rod. Syringe plungers are small parts, and it is desirable not to handle them during layer and assembly operations. The push rod 1270 does not require a layer or special handling, so it is conveniently used for handling the plunger 1258 during processing The syringe plunger 1258 can be placed in a plasma enhanced chemical vapor deposition chamber 1290. At least one of the generally circular front portion 1262 and the generally circular back portion 1268 (here both) is masked, as with the mask 1292 or the seat 1294 shown in FIG. 29, at least substantially without masking at least a generally cylindrical side portion 1266 of the syringe plunger 1258.

The side portion 1266 of the syringe plunger 1258 is contacted with a layer forming reactive gas. Plasma is formed in the deposition chamber 1290 adjacent to the side portion 1266 of the syringe plunger 1258. A layer 1296 is deposited selectively on the side portion 1266 of the syringe plunger 1258, using plasma enhanced chemical vapor deposition.

FIG. 29 thus shows apparatus useful for carrying out a method for selectively layer a side portion 1266 of a generally cylindrical article 1302 using plasma enhanced chemical vapor deposition. The method can include several steps. A generally cylindrical article 1258 is provided having opposed end portions 1262, 1268 and a generally cylindrical side portion 1266. The article 1258 is placed in a plasma enhanced chemical vapor deposition chamber 1290. At least a portion of at least one of the end portions 1262 and 1268, here both, is masked, while leaving a side portion 1266 unmasked. At least one layer 1296 is selectively deposited on the unmasked side portion 1266 of the article 1258 by plasma enhanced chemical vapor deposition of a layer forming precursor.

Optionally, less than all of the end portion 1262 of the generally cylindrical article 1258 can be coated. This can be accomplished, for example, by providing a mask 1292 that does not cover some parts of the end portion 1262. For example, a central end portion of the generally cylindrical article 1258 can be coated and a peripheral end portion 1278 of the generally cylindrical article 1258 can remain uncoated by suitable selection and placement of the mask 292.

In the embodiment of FIGS. 29-30, the apparatus is configured to coat the side portion 1266 of the generally cylindrical article 1258 adjacent to the end portion 1262. Optionally, however, the apparatus can be arranged, as by extending a skirt down from the mask 1292, to mask a side portion which is the adjacent or upper part of the side portion 1266, or alternatively to mask all of the side portion 1266.

In another modification, a side portion 1296 of the generally cylindrical article 1258 distal from the adjacent portion, lower in the orientation of FIG. 29, can remain uncoated. This can be carried out, for example, by extending the mask and support 1294 up against the lower part 1296, or alternatively against all, of the side portion 1266.

Referring now to the embodiment of FIGS. 31 and 32, apparatus analogous to that of FIG. 27 is shown for layer another type of vessel closure, here a simple stopper 1302 as might be used for a urine sample tube or a vial.

FIG. 33 shows apparatus for selectively layer the side portion 1316 of a septum 1310, which is a special purpose stopper for permanently stopping a drug vial or other vessel. In this instance, the generally cylindrical article 1310 is a vessel septum. The septum 1310 is contoured on its end portions 1312 and 1320, and has a thin web 1322 adapted to be pierced with a hypodermic needle to withdraw the contents of the vessel without unsealing the vessel. The web 1322 yields to piercing by a needle, then the pierced portion closes back up to reseal the vessel when the needle is withdrawn.

The side portion 1316 is selectively coated by subjecting it to PECVD while masked with one or more of a mask 1324 covering a central end portion 1312, a mask 1326 covering the end portion 1320 and the adjacent side portion 1330, and a mask 1328 covering the peripheral end portion 1332. The side portion 1316 adjacent to the central end portion 1312 and further away from the peripheral end portion 1332 is uncovered and can be coated in a chamber of PECVD apparatus surrounding the structure shown in FIG. 33. As is conventional, vent passages can be provided, such as the vent passage 1334 or a porous mask, to allow air pockets trapped between the article to be coated and the masks to be vented when vacuum is drawn on the masked article.

The mask 1324 has a portion 1336 configured for mating with an end portion 1312 of the septum or other generally cylindrical article 1310. Similarly, the mask 1326 has a portion 1336 configured for mating with an end portion 1320 of the septum or generally cylindrical article 1310. The mask 1326 and the end portion 1320 of the generally cylindrical article 1310 have substantially identical mating portions, touching throughout. The mask 1324, however, does not have a substantially identical mating portion compared to the end portion 1312, however, as the end portion 1312 is annular, surrounding a recess which does not follow or mate with the mask 1324.

Optionally, the holder or mask 1326 can have more than one portion or opening such as 1336 to receive plural or multiple generally cylindrical articles, so all can be coated in the PECVD apparatus at once. The mask 1326 can have a surface 1340 having multiple wells 1336 configured to receive and mask multiple generally cylindrical articles 1310 for at least one layer such as 1318.

The multiple wells or openings can form a pattern to receive multiple generally cylindrical articles for at least one layer. Optionally, the masks such as 1324 and 1328 can be repeated, and optionally can be joined together to form a template having the masks registered with the openings in the holder.

Similarly, the mask 1292 and holder 1294 of FIG. 29 can be multiplied to treat multiple generally cylindrical articles 1258 at the same time in one deposition step.

FIGS. 31 and 32 illustrate that the generally cylindrical article 1282 can be a vessel stopper that is retained in the stopper holder 1080 with its shoulder preventing the stopper 1282 from advancing past its seated position (as illustrated) when vacuum is drawn.

An assembly of the generally cylindrical article 1282 with a vessel is contemplated. The generally cylindrical article 1282 is configured to function as a stopper for the vessel.

FIGS. 34-35 show an embodiment of a medical sample tube, such as an evacuated blood collection tube, in which the generally cylindrical article 1282 is a stopper of a vessel closure 1302, for example an assembly of a vessel stopper 1282 and shield 1304. In this embodiment, optionally the vessel stopper and shield assembly 1302 can be positioned with a stopper end portion 1306 within the bore 1300 (FIG. 35) and the shield 1304 at least partially outside the bore 1300.

An assembly of the generally cylindrical article 1282 with a vessel 1308 and a shield 1304 is contemplated as shown in FIG. 35, wherein the generally cylindrical article 1282 is configured to function as a stopper for the vessel 1308. The vessel 1308 optionally further comprises a PECVD treated interior portion 1408.

Alternatively, the vessel can be a vial or a cuvette. The vial or cuvette can further comprise a PECVD treated interior portion.

In any embodiment, before depositing a layer, the portions of the generally cylindrical article to be coated can be exposed to a partial vacuum to extract or harden displaceable fluid material from the generally cylindrical article. Also or instead, the portions of the generally cylindrical article to be coated can be exposed to PECVD pretreatment, as with oxygen, to oxidize or otherwise treat the surface to be coated or to oxidize any displaceable fluid material removed from the generally cylindrical article. This treatment can be limited to the areas to be coated, or it can be a more general treatment before the generally cylindrical article is masked or installed in a bore.

In any embodiment, any desired type or conditions of PECVD layer can be used or applied. For example, the at least one layer can comprise or function as a barrier layer, for example of SiOx as defined below, to reduce leaching of material from the generally cylindrical article through the coated portion. The at least one layer can comprise or function as a barrier layer, for example of SiOx as defined below, to reduce leaching of material into the generally cylindrical article through the coated end portion.

The at least one layer can be a hydrophobic layer 1280 having an atomic ratio of Si to O to C of $Si_wO_xC_y$, as defined below, adapted to provide the coated portion with the desired surface hydrophobicity for contact with a material to which the at least one layer will be exposed. For example, a hydrophobic layer can be used on the portions of a plunger 1258, stopper 1282, or septum 1310 that will be exposed to a pharmaceutical preparation, for example to passivate the coated surface or to allow the contents of a syringe or stoppered vessel to be more fully removed without adhering to or precipitating on the coated surface. Another use for the hydrophobic layer is to prevent coagulation or clotting activation of blood received in an evacuated blood collection tube 1308 on the exposed surfaces of the stopper 1282

The at least one layer can be a barrier against the ingress of an atmospheric gas or fluid through the coated portion or a barrier against the escape of a material through the coated portion. Such a barrier layer typically will be made of $SiO_x$ as defined below.

The at least one layer can comprises more than one of a leaching barrier, a hydrophobicity layer, a passivation layer, a barrier against ambient conditions, or a barrier against escape of contents, and more than one layer with different properties can be applied.

For example, for a prefilled syringe or a stopped vessel (stopped with a stopper or a septum), it may be useful to apply one or more of:

a leaching barrier to prevent the contents of the syringe or stopped vessel or another layer from leaching into the plunger or vice versa, a barrier against escape of contents to keep the material in the syringe from losing any volatile constituents, and a hydrophobicity layer to prevent precipitation or other adverse effects on the contents of the syringe or stopped vessel.

Thus, plural layers can be deposited. For example, a first layer having a composition and properties is deposited, following which a second layer having a different composition, different properties, or both can be deposited. Or, a first layer having a composition and properties can be deposited, following which a second layer having the same composition and properties can be deposited. Alternatively, a first layer having a composition and properties can be deposited, following which a second layer having a different composition, properties, or both can be deposited, following which a third layer having the same composition and properties as the first layer comprises can be deposited. Still another option is that a first layer having a composition and properties can be deposited, following which plural layers of a second layer having a different composition, properties, or both than the first layer can be deposited, following which a third layer having the same composition and properties as the first layer can be deposited.

The lubricity layer is produced from a PECVD process using the following process gas and input power:

an precursor gas that reacts to form a layer, optionally oxygen or another oxidizing agent, a carrier gas such as argon or helium, and sufficient plasma generation power input to induce layer formation.

The materials and conditions used can be effective to reduce the sliding force or breakout force of the generally cylindrical object at least 25 percent relative to an uncoated syringe barrel.

In any embodiment, the layer forming reactive gas used for PECVD can be an organometallic precursor gas.

The precursor for the PECVD layer of the present invention is broadly defined as an organometallic precursor. An organometallic precursor is defined in this specification as comprehending compounds of metal elements from Group III and/or Group IV of the Periodic Table having organic residues, e.g. hydrocarbon, aminocarbon or oxycarbon residues. Organometallic compounds as presently defined include any precursor having organic moieties bonded to silicon or other Group III/IV metal atoms directly, or optionally bonded through oxygen or nitrogen atoms. The relevant elements of Group III of the Periodic Table are Boron, Aluminum, Gallium, Iridium, Thallium, Scandium, Yttrium, and Lanthanum, Aluminum and Boron being preferred. The relevant elements of Group IV of the Periodic Table are Silicon, Germanium, Tin, Lead, Titanium, Zirconium, Hafnium, and Thorium, with Silicon and Tin being preferred. Other volatile organic compounds can also be contemplated. However, organosilicon compounds are preferred for performing present invention.

An organosilicon precursor is contemplated, where an "organosilicon precursor" is defined throughout this specification most broadly as a compound having at least one of the linkages:

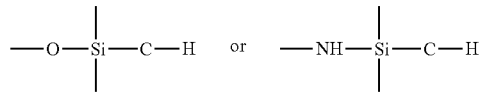

The first structure immediately above is a tetravalent silicon atom connected to an oxygen atom and an organic carbon atom (an organic carbon atom being a carbon atom bonded to at least one hydrogen atom). The second structure immediately above is a tetravalent silicon atom connected to an —NH— linkage and an organic carbon atom (an organic carbon atom being a carbon atom bonded to at least one hydrogen atom). Optionally, the organosilicon precursor is selected from the group consisting of a linear siloxane, a monocyclic siloxane, a polycyclic siloxane, a polysilsesquioxane, a linear silazane, a monocyclic silazane, a polycyclic silazane, a polysilsesquiazane, and a combination of any two or more of these precursors. Also contemplated as a precursor, though not within the two formulas immediately above, is an alkyl trimethoxysilane.

If an oxygen-containing precursor (e.g. a siloxane) is used, a representative predicted empirical composition resulting from PECVD under conditions forming a hydrophobic or lubricating layer would be an atomic ratio of Si to O to C of $Si_wO_xC_y$, in which w is 1, x in this formula is from about 0.5 to 2.4, and y is from about 0.6 to about 3, while a representative predicted empirical composition resulting from PECVD under conditions forming a barrier layer would be SiOx, where x in this formula is from about 1.5 to about 2.9. If a nitrogen-containing precursor (e.g. a silazane) is used, the predicted composition would be $Si_{w*}N_{x*}C_{y*}$, i.e. in $Si_wO_xC_y$, O is replaced by N and the indices are adapted to the higher valency of N as compared to O (3 instead of 2). The latter adaptation will generally follow the ratio of w, x, y in a siloxane to the corresponding indices in its aza counterpart. In a particular aspect of the invention, $Si_{w*}N_{x*}C_{y*}$ in which w*, x*, y* are defined the same as w, x, y for the siloxane counterparts, but for an optional deviation in the number of hydrogen atoms.

One type of precursor starting material having the above empirical formula is a linear siloxane, for example a material having the following formula:

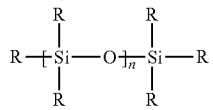

in which each R is independently selected from alkyl, for example methyl, ethyl, propyl, isopropyl, butyl, isobutyl, t-butyl, vinyl, alkyne, or others, and n is 1, 2, 3, 4, or greater, optionally two or greater. Several examples of contemplated linear siloxanes are hexamethyldisiloxane (HMDSO),
octamethyltrisiloxane,
decamethyltetrasiloxane,
dodecamethylpentasiloxane,
or combinations of two or more of these. The analogous silazanes in which —NH— is substituted for the oxygen atom in the above structure are also useful for making analogous layers. Several examples of contemplated linear silazanes are octamethyltrisilazane, decamethyltetrasilazane, or combinations of two or more of these.

V.C. Another type of precursor starting material is a monocyclic siloxane, for example a material having the following structural formula:

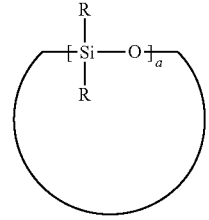

in which R is defined as for the linear structure and "a" is from 3 to about 10, or the analogous monocyclic silazanes. Several examples of contemplated hetero-substituted and unsubstituted monocyclic siloxanes and silazanes include 1,3,5-trimethyl-1,3,5-tris(3,3,3-trifluoropropyl)methyl] cyclotrisiloxane
2,4,6,8-tetramethyl-2,4,6,8-tetravinylcyclotetrasiloxane,
pentamethylcyclopentasiloxane,
pentavinylpentamethylcyclopentasiloxane,
hexamethylcyclotrisiloxane,
hexaphenylcyclotrisiloxane,
octamethylcyclotetrasiloxane (OMCTS),
octaphenylcyclotetrasiloxane,
decamethylcyclopentasiloxane
dodecamethylcyclohexasiloxane,
methyl(3,3,3-trifluoropropl)cyclosiloxane,
Cyclic organosilazanes are also contemplated, such as
Octamethylcyclotetrasilazane,
1,3,5,7-tetravinyl-1,3,5,7-tetramethylcyclotetrasilazane
hexamethylcyclotrisilazane,
octamethylcyclotetrasilazane,
decamethylcyclopentasilazane,
dodecamethylcyclohexasilazane, or
combinations of any two or more of these.

V.C. Another type of precursor starting material is a polycyclic siloxane, for example a material having one of the following structural formulas:

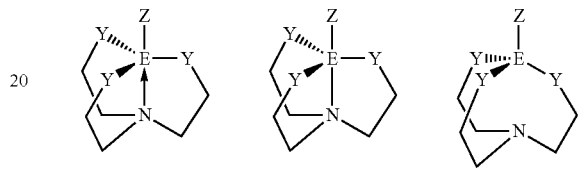

in which Y can be oxygen or nitrogen, E is silicon, and Z is a hydrogen atom or an organic substituent, for example alkyl such as methyl, ethyl, propyl, isopropyl, butyl, isobutyl, t-butyl, vinyl, alkyne, or others. When each Y is oxygen, the respective structures, from left to right, are a silatrane, a silquasilatrane, and a silproatrane. When Y is nitrogen, the respective structures are an azasilatrane, an azasilquasiatrane, and an azasilproatrane.

V.C. Another type of polycyclic siloxane precursor starting material is a polysilsesquioxane, with the empirical formula $RSiO_{1.5}$ and the structural formula:

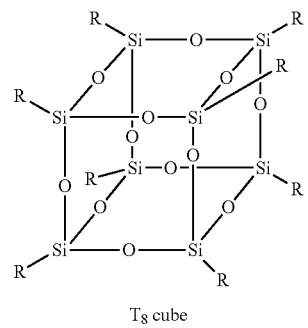

$T_8$ cube in which each R is a hydrogen atom or an organic substituent, for example alkyl such as methyl, ethyl, propyl, isopropyl, butyl, isobutyl, t-butyl, vinyl, alkyne, or others. Two commercial materials of this sort are a $T_8$ cube in which each R is methyl, and a $T_8$ cube in which 90% of the R groups are methyl, 10% are hydrogen atoms. This material is available in a 10% solution in tetrahydrofuran, for example. Combinations of two or more of these are also contemplated. Other examples of a contemplated precursor are methylsilatrane, CAS No. 2288-13-3, in which each Y is oxygen and Z is methyl, methylazasilatrane, SST-eM01 poly(methylsilsesquioxane), in which each R optionally can be methyl, SST-3MH1.1 poly(Methyl-Hydridosilsesquioxane), in which 90% of the R groups are methyl and 10% are hydrogen atoms, or a combination of any two or more of these.

V.C. The analogous polysilsesquiazanes in which —NH— is substituted for the oxygen atom in the above structure are also useful for making analogous layers. Examples of contemplated polysilsesquiazanes are a poly (methylsilsesquiazane), in which each R is methyl, and a poly(Methyl-Hydridosilsesquiazane, in which 90% of the R groups are methyl, 10% are hydrogen atoms. Combinations of two or more of these are also contemplated.

V.C. One particularly contemplated precursor for the lubricity layer according to the present invention is a monocyclic siloxane, for example is octamethylcyclotetrasiloxane.

One particularly contemplated precursor for the barrier layer according to the present invention is a linear siloxane, for example is HMDSO.

The lubricity layer or layer can be less than 1000 nm thick, applied by plasma-enhanced chemical vapor deposition. It is useful on the side surface of a plunger or stopper that slides against an adjacent vessel or syringe barrel wall when the syringe is operated or the vessel is stopped or unstopped.

In one option, the lubricity layer comprises:

a layer having an atomic ratio of Si to O/N to C of $Si_wO_xC_y$ or $Si_wN_xC_y$ in which w is 1, x in this formula is from about 0.5 to 2.4, and y is from about 0.6 to about 3; and a surface treatment covering the lubricity layer in an amount effective to reduce the leaching of the lubricity layer, the thermoplastic base material of the vessel, or both, into the lumen.

The lubricity layer and surface treatment can be composed, and present in relative amounts, effective to provide a breakout force (the force to start the stationary plunger or stopper moving), sliding force (the force needed to keep the moving plunger or stopper in motion), or both less than the corresponding force required in the absence of the lubricity layer and surface treatment. A lubricity layer can also be applied without the surface treatment.

The lubricity layer can be formed by employing a gaseous reactant or process gas having a standard volume ratio of, from 1 to 6 standard volumes of the precursor,
from 5 to 100 standard volumes of a carrier gas, and
from 0.1 to 2 standard volumes of an oxidizing agent.

Alternatively, from 2-4 standard volumes (for example, standard cubic centimeters per minute or sccm) of the precursor can be used in the process gas. Alternatively, from 10-70 standard volumes of the carrier gas can be used in the process gas. Alternatively, from 0.5 to 1.5 standard volumes of the oxidizing agent can be used in the process gas. Alternatively, from 0.8 to 1.2 standard volumes of the oxidizing agent can be used in the process gas. Any gas composition specified in U.S. Ser. No. 61/413,334, filed Nov. 12, 2010, or PCT/US11/36097, filed May 11, 2011, can also be used. These applications are incorporated by reference in their entirety herein.

The flow rate of the organosilicon precursor during PECVD can be equal to or less than 6 sccm, optionally equal to or less than 2.5 sccm, optionally equal to or less than 1.5 sccm, optionally equal to or less than 1.25 sccm.

The plasma can be formed by exciting the reaction mixture with electromagnetic energy, which can be radio frequency energy or microwave energy, for two examples. In a small vessel such as the syringe of FIG. 26 a medical sample tube such as that of FIG. 34, or a vial containing an injectable medication, typically containing from a fraction of a mL to 10 mL of volume, PECVD can be carried out, for example, with a plasma made by energizing the vicinity of the precursor with electrodes supplied with electric power at from 1 to 22 Watts, for example, set to provide the desired results. The precursor can be contacted with a plasma made by energizing the vicinity of the precursor with electrodes supplied with electric power at less than 10 W/ml., alternatively from 5 W/ml to 0.1 W/ml, alternatively from 4 W/ml. to 0.1 W/ml., alternatively from 2 W/ml to 0.2 W/ml. of plasma volume.

V.C. In any of the layer methods according to the present invention, the applying step optionally can be carried out by vaporizing the precursor and providing it in the vicinity of the substrate. E.g., OMCTS is usually vaporized by heating it to about 50° C. before applying it to the PECVD apparatus.

In the context of the present invention, the following PECVD method is generally applied, which contains the following steps:

(a) providing a gaseous reactant comprising a precursor as defined herein, optionally an organosilicon precursor, and optionally O2 in the vicinity of the substrate surface; and (b) generating a plasma from the gaseous reactant, thus forming a layer on the substrate surface by plasma enhanced chemical vapor deposition (PECVD).

In the method, the layer characteristics are advantageously set by one or more of the following conditions: the plasma properties, the pressure under which the plasma is applied, the power applied to generate the plasma, the presence and relative amount of O2 in the gaseous reactant, the plasma volume, and the organosilicon precursor. Optionally, the layer characteristics are set by the presence and relative amount of O2 in the gaseous reactant and/or the power applied to generate the plasma.

In all embodiments of the present invention, the plasma is in an optional aspect a non-hollow-cathode plasma.

In a further preferred aspect, the plasma is generated at reduced pressure (as compared to the ambient or atmospheric pressure). Optionally, the reduced pressure is less than 300 mTorr, optionally less than 200 mTorr, even optionally less than 100 mTorr.

The PECVD optionally is performed by energizing the gaseous reactant containing the precursor with electrodes powered at a frequency at microwave or radio frequency, and optionally at a radio frequency. The radio frequency preferred to perform an embodiment of the invention will also be addressed as "RF frequency". A typical radio frequency range for performing the present invention is a frequency of from 10 kHz to less than 300 MHz, optionally from 1 to 50 MHz, even optionally from 10 to 15 MHz. A frequency of 13.56 MHz is most preferred, this being a government sanctioned frequency for conducting PECVD work.

There are several advantages for using a RF power source versus a microwave source: Since RF operates a lower power, there is less heating of the substrate/vessel. Because the focus of the present invention is putting a plasma layer on plastic substrates, lower processing temperature are desired to prevent melting/distortion of the substrate. To prevent substrate overheating when using microwave PECVD, the microwave PECVD is applied in short bursts, by pulsing the power. The power pulsing extends the cycle time for the layer, which is undesired in the present invention. The higher frequency microwave can also cause off-gassing of volatile substances like residual water, oligomers and other materials in the plastic substrate. This offgassing can interfere with the PECVD layer. A major concern with using microwave for PECVD is delamination of the layer from the substrate. Delamination occurs because the microwaves change the surface of the substrate prior to depositing the layer layer. To mitigate the possibility of delamination, interface layer layers have been developed for microwave PECVD to achieve good bonding between the layer and the substrate. No such interface layer layer is needed with RF PECVD as there is no risk of delamination. Finally, the lubricity layer and hydrophobic layer according to the present invention are advantageously applied using lower power. RF power operates at lower power and provides more control over the PECVD process than microwave power. Nonetheless, microwave power, though less preferred, is usable under suitable process conditions.

Furthermore, for all PECVD methods described herein, there is a specific correlation between the power (in Watts) used to generate the plasma and the volume of the lumen wherein the plasma is generated. Typically, the lumen is the lumen of a vessel coated according to the present invention. The RF power should scale with the volume of the vessel if the same electrode system is employed. Once the composition of a gaseous reactant, for example the ratio of the precursor to O2, and all other parameters of the PECVD layer method but the power have been set, they will typically not change when the geometry of a vessel is maintained and only its volume is varied. In this case, the power will be directly proportional to the volume. Thus, starting from the power to volume ratios provided by present description, the power which has to be applied in order to achieve the same or a similar layer in a vessel of same geometry, but different size, can easily be found. The influence of the vessel geometry on the power to be applied is illustrated by the results of the Examples for tubes in comparison to the Examples for syringe barrels.

For any layer of the present invention, the plasma is generated with electrodes powered with sufficient power to form a layer on the substrate surface. For a lubricity layer or hydrophobic layer, in the method according to an embodiment of the invention the plasma is optionally generated (i) with electrodes supplied with an electric power of from 0.1 to 25 W, optionally from 1 to 22 W, optionally from 3 to 17 W, even optionally from 5 to 14 W, optionally from 7 to 11 W, for example of 8 W; and/or (ii) wherein the ratio of the electrode power to the plasma volume is less than 10 W/ml, optionally is from 5 W/ml to 0.1 W/ml, optionally is from 4 W/ml to 0.1 W/ml, optionally from 2 W/ml to 0.2 W/ml. For a barrier layer or SiOx layer, the plasma is optionally generated (i) with electrodes supplied with an electric power of from 8 to 500 W, optionally from 20 to 400 W, optionally from 35 to 350 W, even optionally from 44 to 300 W, optionally from 44 to 70 W; and/or (ii) the ratio of the electrode power to the plasma volume is equal or more than 5 W/ml, optionally is from 6 W/ml to 150 W/ml, optionally is from 7 W/ml to 100 W/ml, optionally from 7 W/ml to 20 W/ml.

The power (in Watts) used for PECVD has an influence on the layer properties. Typically, an increase of the power will increase the barrier properties of the layer, and a decrease of the power will increase the lubricity and hydrophobicity of the layer. E.g., for a layer on the inner wall of syringe barrel having a volume of about 3 ml, a power of less than 30 W will lead to a layer which is predominantly a barrier layer, while a power of more than 30 W will lead to a layer which is predominantly a lubricity layer.

A further parameter determining the layer properties is the ratio of $O_2$ (or another oxidizing agent) to the precursor (e.g. organosilicon precursor) in the gaseous reactant used for generating the plasma. Typically, an increase of the $O_2$ ratio in the gaseous reactant will increase the barrier properties of the layer, and a decrease of the $O_2$ ratio will increase the lubricity and hydrophobicity of the layer.

If a lubricity layer is desired, then $O_2$ is optionally present in a volume-volume ratio to the gaseous reactant of from 0:1 to 5:1, optionally from 0:1 to 1:1, even optionally from 0:1 to 0.5:1 or even from 0:1 to 0.1:1. If, on the other hand, a barrier or SiOx layer comprises desired, then the $O_2$ is optionally present in a volume:volume ratio to the gaseous reactant of from 1:1 to 100:1 in relation to the silicon containing precursor, optionally in a ratio of from 5:1 to 30:1, optionally in a ratio of from 10:1 to 20:1, even optionally in a ratio of 15:1.

The contemplated hydrophobicity layer can be applied using the same process apparatus and ingredients under different conditions, optionally with the same precursor or a different precursor selected from those provided above for the lubricity layer. The hydrophobic characteristics of the layer are set by setting the ratio of the $O_2$ to the organosilicon precursor in the gaseous reactant, and/or by setting the electric power used for generating the plasma.

The resulting layer optionally has a lower wetting tension than the uncoated surface. For example, the layer can have a wetting tension of from 20 to 72 dyne/cm, alternatively from 30 to 60 dynes/cm, alternatively from 30 to 40 dynes/cm, alternatively 34 dyne/cm. The layer optionally can be more hydrophobic than the uncoated surface.

The at least one layer optionally comprises a barrier layer. The contemplated barrier layer or layer can be applied using the same process apparatus and ingredients as above under different conditions, optionally with the same precursor or a different precursor selected from those provided above for the lubricity layer. The barrier characteristics of the layer are set by setting the ratio of the $O_2$ to the organosilicon precursor in the gaseous reactant, and/or by setting the electric power used for generating the plasma.

One example of a suitable barrier layer is one or more layers of SiOx, in which x is from 1.5 to 2.9, from 5 to 200 nm thick.

Typically, an increase of the power will increase the barrier properties of the layer. For a layer on the inner wall of syringe barrel having a volume of about 3 ml, a power of more than 30 W will lead to a layer which is predominantly a lubricity layer.

A further parameter determining the layer properties is the ratio of $O_2$ (or another oxidizing agent) to the precursor (e.g. organosilicon precursor) in the gaseous reactant used for generating the plasma. Typically, an increase of the $O_2$ ratio in the gaseous reactant will increase the barrier properties of the layer.

If a barrier or SiOx layer is desired, then the $O_2$ is optionally present in a volume:volume ratio to the gaseous reactant of from 1:1 to 100:1 in relation to the silicon containing precursor, optionally in a ratio of from 5:1 to 30:1, optionally in a ratio of from 10:1 to 20:1, even optionally in a ratio of 15:1.

V.A. A specific embodiment is a method of applying a barrier layer of SiOx, defined in this specification (unless otherwise specified in a particular instance) as a layer containing silicon, oxygen, and optionally other elements, in which x, the ratio of oxygen to silicon atoms, is from about 1.5 to about 2.9, or 1.5 to about 2.6, or about 2. These alternative definitions of x apply to any use of the term SiOx in this specification.

V.A. Plasma formed in the reaction mixture preferably is substantially free of hollow cathode plasma. The vessel wall is contacted with the reaction mixture, and the layer of SiOx is deposited on at least a portion of the vessel wall.

V.A. In certain embodiments, the generation of a uniform plasma throughout the portion of the vessel to be coated is contemplated, as it has been found in certain instances to generate an SiOx layer providing a better barrier against oxygen. Uniform plasma means regular plasma that does not include a substantial amount of hollow cathode plasma (which has a higher emission intensity than regular plasma and is manifested as a localized area of higher intensity interrupting the more uniform intensity of the regular plasma).

V.A. The hollow cathode effect is generated by a pair of conductive surfaces opposing each other with the same negative potential with respect to a common anode. If the spacing is made (depending on the pressure and gas type) such that the space charge sheaths overlap, electrons start to oscillate between the reflecting potentials of the opposite wall sheaths leading to multiple collisions as the electrons are accelerated by the potential gradient across the sheath region. The electrons are confined in the space charge sheath overlap which results in very high ionization and high ion density plasmas. This phenomenon is described as the hollow cathode effect. Those skilled in the art are able to vary the processing conditions, such as the power level and the feed rates or pressure of the gases, to form uniform plasma throughout or to form plasma including various degrees of hollow cathode plasma.

Another suitable barrier layer is a composite of different layers, for example, comprising:

an inner layer of SiOx, in which x is from 1.5 to 2.9, from 5 to 200 nm thick, having an inside surface facing the lumen and an outside surface;

a spacer layer from 100 nm to 3 mm thick having an inside surface and an outside surface, the inside surface facing the inner layer of SiOx; and an outer layer of SiOx, in which x is from 1.5 to 2.9, from 5 to 200 nm thick, having an inside surface facing the spacer layer and an outside surface.

The outer layer of SiOx can be made from an organosilicon compound precursor as described above, for example hexamethyldisiloxane, and the PECVD conditions described above for barrier layers or layers.

The spacer layer can be made from an organosilicon compound precursor as described above, for example hexamethyldisiloxane, applied at an oxidizing gas:precursor volumetric flow ratio (sccm) of from 4:1 to 8:1. The spacer layer can be formed by radio frequency (RF) PECVD of a reaction mixture comprising an organosilicon precursor and an oxidizing gas at an RF power level of from 10 to 50 Watts, preferably from 20 to 40 Watts, preferably from 25 to 35 Watts. Scaled to the volume of the holder or vessel, RF power can be applied at a level of from 1-10, preferably from 2-7, preferably from 3 to 5 Watts per mL of lumen void volume.

The spacer layer can be a composite of at least two PECVD applied layers, sequentially applied, allowing enough time for cooling between layers to prevent distortion of the generally cylindrical article. For example, the spacer layer can be a composite of at least 10 PECVD applied layers, alternatively at least 20 PECVD applied layers.

Plasma Layer Deposition

The new plasma layer technology discussed herein is based on Plasma Enhanced Chemical Vapor Deposition (PECVD). The process utilizes a silicon containing vapor that can be combined with oxygen at reduced pressures (mTorr range–atmospheric pressure is 760 Torr) inside a blood tube or syringe. An electrical field generated at 13.56 MHz [radio frequency range] is then applied between an external electrode and an internal grounded gas inlet to create a plasma. At the pressures and powers that are used to coat tubes and syringes, the plasma process is driven by electron impact ionization, which means the electrons in the process are the driving force behind the chemistry. Specifically, the plasma drives the chemical reaction through electron impact ionization of the silicon containing material [hexamethyldisiloxane (HMDSO and other reactants like octamethylcyclotretrasiloxane (OMCTS)] resulting in a silicon dioxide or SiOxCy layer deposited onto the interior surfaces of the tube or syringe. These layers are on the order of 20 or more nanometers in thickness. HMDSO consists of an Si—O—Si backbone with six (6) methyl groups attached to the silicon atoms. The process breaks the Si—C bonds and (at the surface of the tube or syringe) reacts with oxygen to create silicon dioxide. Since the layer is grown on an atomic basis, dense, conformal layers with thicknesses of 20-30 nanometers can achieve significant barrier properties. The silicon oxide acts as a physical barrier to gases, moisture, and small organic molecules, and is of greater purity than commercial glasses. OMCTS results in layers with lubricity or anti-adhesion properties.

The new technology is unique in several aspects:

1. The process utilizes the rigid container, such as the vessel holder 1050, as the vacuum chamber. PECVD conventionally uses a secondary vacuum vessel into which the part(s) are loaded and coated. Utilizing the container as a vacuum chamber significantly simplifies the process apparatus and reduces cycle/processing time, and thus manufacturing cost and capital. This approach also reduces scale-up issues since scale-up is as simple as replicating the number of tubes or syringes required to meet the throughput requirements.

2. Radio Frequency excitation of the plasma allows energy to be imparted to the ionized gas with little heating of the part. Unlike microwave excitation energies, typically used in PECVD, which will impart significant energy to water molecules in the part itself, radio frequency will not preferentially heat the polymeric tubes or syringes. Controlled heat absorption is critical to prevent substrate temperature increases approaching plastic glass transition temperatures, causing loss of dimensional integrity (collapse under vacuum).

3. Single layer gas barrier layer—the new technology utilizes a single layer of silicon dioxide directly on the interior surface of the part. Most other barrier technologies (thin film) require at least two layers.

4. Combination barrier-lubricity layers—the new technology utilizes a combination silicon dioxide/SiOxCy layer to provide multiple performance attributes (barrier/lubricity).

5. Gas inlet/electrode configuration—the highly asymmetric design helps to prolong the gas inlet life.

The plasma deposition technology utilizes a simple manufacturing configuration. The system is based on a "puck" or vessel holder 1050, shown for example in FIG. 27, which is used in transportation of tubes, syringes, and plunger holders 1080, in and out of the layer station. The device-puck interface (see FIGS. 1 and 2, of U.S. Publ. Appl U.S. Publ. Appl. No. 2010/0298738 A1, published Nov. 25, 2010, issued as U.S. Pat. No. 7,985,188 on Jul. 26, 2011. The latter publication and patent are incorporated here by reference) is useful, since once layer/characterization conditions are established at the pilot scale, there are no scaling issues when moving to full scale production; one simply increases the number of pucks through the same process. The puck is manufactured from a polymeric material (e.g. Delrin™) to provide an electrically insulated base. The tube and syringe are mounted into the puck with the largest opening sealing against an o-ring (mounted in the puck itself). The o-ring provides the vacuum seal between the part and the puck so that the ambient air (principally nitrogen and oxygen with some water vapor) can be removed (pressure reduced) and the process gases introduced. The puck has several key features in addition to the o-ring seal. The puck provides a means of connection to the vacuum pump (which pumps away the atmospheric gases and the by-products of the silicon dioxide reaction), a means of accurately aligning the gas inlet in the part, and a means of providing a vacuum seal between the puck and gas inlet.

For $SiO_x$ deposition, HMDSO and oxygen gases are then admitted into the plunger holder 1080 through the grounded gas inlet which extends up into the part. At this point, the puck and plunger holder 1080 are moved into the electrode area. The electrode is constructed from a conductive material (for example copper) and provides a tunnel through which the part passes. The electrode does not make physical contact with the plunger holder 1080 or the puck and is supported independently. An RF impedance matching network and power supply are connected directly to the electrode. The power supply provides energy (at 13.56 MHz) to the impedance matched network. The RF matching network acts to match the output impedance of the power supply to the complex (capacitive and inductive) impedance of the ionized gases. The matching network delivers maximum power delivery to the ionized gas which ensures deposition of the silicon dioxide layer.

Once the plunger holder 1080 is coated (as the puck moves the plunger holder 1080 through the electrode channel—which is stationary), the gases are stopped and atmospheric air (or pure nitrogen) is allowed inside the puck/plunger holder 1080 to bring it back to atmospheric pressure. At this time, the plunger holder 1080 can be removed from the puck and moved to the next processing station.

The above describes clearly the means of layer a blood tube, parenteral vial or ampule, as well as a plunger 1258, stopper 1282, septum 1310, or other articles. Syringes require an additional step before and after loading onto the puck. Since the syringes have opening at both ends (one for connection to a needle and the second for installation of a plunger), the needle end must be sealed prior to layer. The above process allows reaction gases to be admitted into the plastic part interior, an electrical current to pass through the gas inside of the part and a plasma to be established inside the part. The plasma (an ionized composition of the HMDSO or OMCTS and oxygen gases) is what drives the chemistry and the deposition of the plasma layer.

While the preferred embodiments of the invention have been described in detail above, the invention is not limited to the specific embodiments described, which should be considered as merely exemplary.

What is claimed is:

1. A method of molding a barrel configured for storing and dispensing an injectable product, the method comprising:
   providing injection molding equipment including a substantially rigid surface defining a cavity and a substantially rigid core, the cavity and core defining a molding space between them, at least one of the cavity and the core being movable with respect to the other along a parting axis to open the molding space for removing a molded barrel, at least one portion of the core being a low draft element having a draft angle of from 0.01° to 0.16° with respect to the parting axis;
   injecting a thermoplastic fluid molding material into the molding space, the molding material being selected from the group consisting of: olefin polymer, polypropylene (PP), polyethylene (PE), cyclic olefin copolymer (COC), cyclic olefin polymer (COP) and a combination of two or more of the foregoing;
   forming at least a surface of the fluid molding material against the low draft element to define a low draft formed surface;
   solidifying at least the low draft formed surface to provide a solid low draft formed surface;
   creating a clearance between the low draft element and the low draft formed surface sufficiently to release the low draft element from the low draft formed surface;
   parting the cavity and core along the parting axis; and
   removing the barrel from the molding space without causing defects on the barrel, the barrel comprising an open end, a dispensing opening and a generally cylindrical sidewall, the barrel being configured to have a piston movably seated therein and which is axially slidable in the barrel for dispensing an injectable product contained in the barrel out the dispensing opening.

2. The method of claim 1, further comprising:
   heating at least part of the low draft element to a first selected temperature to expand it; and
   cooling at least part of the low draft element to a second selected average temperature less than the first selected temperature to thermally contract at least a portion of the low draft element away from the solid low draft formed surface to create the clearance.

3. The method of claim 1, in which the low draft element has a draft angle of up to 0.06°.

4. The method of claim 1, in which the low draft element has a draft angle of up to 0.03°.

5. The method of claim 1, in which the low draft element has a draft angle of up to 0.014°.

6. The method of claim 1, in which the low draft element comprises H13 grade steel.

7. The method of claim 1 further comprising, after molding, applying a $SiO_x$ barrier layer on the solid low draft formed surface using a plasma enhanced chemical vapor deposition (PECVD) process, wherein x is from 1.5 to 2.9 and the barrier layer is from 5 to 200 nm thick.

8. A method of molding a barrel configured for storing and dispensing an injectable product, the method comprising:
   providing injection molding equipment including a substantially rigid surface defining a cavity and a substantially rigid core, the cavity and core defining a molding space between them, at least one of the cavity and the core being movable with respect to the other along a parting axis to open the molding space for removing a molded barrel, at least one portion of the core being a low draft element having a draft angle of from 0.01° to 0.16° with respect to the parting axis;
   injecting a thermoplastic fluid molding material into the molding space, wherein the molding material is configured to form a barrel that is clear in appearance;
   forming at least a surface of the fluid molding material against the low draft element to define a low draft formed surface;
   solidifying at least the low draft formed surface to provide a solid low draft formed surface;
   creating a clearance between the low draft element and the low draft formed surface sufficiently to release the low draft element from the low draft formed surface;
   parting the cavity and core along the parting axis; and removing the barrel, which is clear in appearance, from the molding space without causing defects on the barrel, the barrel comprising an open end, a dispensing opening and a generally cylindrical sidewall, the barrel being configured to have a piston movably seated therein and which is axially slidable in the barrel for dispensing an injectable product contained in the barrel out the dispensing opening.

9. The method of claim 8, further comprising:
heating at least part of the low draft element to a first selected temperature to expand it; and
cooling at least part of the low draft element to a second selected average temperature less than the first selected temperature to thermally contract at least a portion of the low draft element away from the solid low draft formed surface to create the clearance.

10. The method of claim 8, in which the low draft element has a draft angle of up to 0.06°.

11. The method of claim 8, in which the low draft element has a draft angle of up to 0.03°.

12. The method of claim 8, in which the low draft element has a draft angle of up to 0.014°.

13. The method of claim 8, in which the molding material comprises cyclic olefin copolymer (COC) and/or cyclic olefin polymer (COP).

14. The method of claim 8 further comprising, after molding, applying a $SiO_x$ barrier layer on the solid low draft formed surface using a plasma enhanced chemical vapor deposition (PECVD) process, wherein x is from 1.5 to 2.9 and the barrier layer is from 5 to 200 nm thick.

15. A syringe assembly comprising:
a barrel including an open end, a dispensing opening and a generally cylindrical side wall, the barrel being made of substantially rigid thermoplastic material that is clear in appearance, defining a bore for containing a liquid, the bore having an axial draft angle ($\theta$) of from 0.01° to 0.16°, wherein the barrel comprises no defects resulting from a process for making the barrel; and
a piston disposed within the bore, the piston having a leading face, a trailing face, and a side edge configured to movably seat in the bore, the piston being axially slidable in the bore for dispensing any liquid contained in the barrel out the dispensing opening.

16. The syringe assembly of claim 15, wherein the rigid thermoplastic material is selected from the group consisting of: olefin polymer, polypropylene (PP), polyethylene (PE), cyclic olefin copolymer (COC), cyclic olefin polymer (COP) and a combination of two or more of the foregoing.

17. The syringe assembly of claim 15, wherein the bore has an axial draft angle ($\theta$) of up to 0.06°.

18. The syringe assembly of claim 15, wherein the bore has an axial draft angle ($\theta$) of up to 0.03°.

19. A syringe assembly comprising:
a barrel including a generally cylindrical side wall, the side wall being made of substantially rigid thermoplastic material that is clear in appearance, defining a bore for containing a liquid, the bore having an axial draft angle ($\theta$) of from greater than 0° to 0.16°, wherein the barrel comprises no defects resulting from a process for making the barrel; and a piston disposed within the bore, the piston having a leading face, a trailing face, and a side edge configured to movably seat in the bore, the bore comprising a $SiO_x$ barrier layer applied thereon, wherein x is from 1.5 to 2.9 and the barrier layer is from 5 to 200 nm thick.

20. The syringe assembly of claim 19, in which the rigid thermoplastic material comprises cyclic olefin copolymer (COC) and/or cyclic olefin polymer (COP) and the bore has an axial draft angle ($\theta$) of up to 0.06°.

* * * * *